US012594228B2

(12) United States Patent
Rha et al.

(10) Patent No.: US 12,594,228 B2
(45) Date of Patent: Apr. 7, 2026

(54) COMPOSITION FOR HAIR PROTECTION OR HAIR STRENGTHENING

(71) Applicant: AMOREPACIFIC CORPORATION, Seoul (KR)

(72) Inventors: Chan Su Rha, Yongin-si (KR); Byeonggyu In, Yongin-si (KR); Soo Jin Lee, Yongin-si (KR); Chang Jo Jung, Yongin-si (KR); Byoung Young Woo, Yongin-si (KR); Kilsun Myoung, Yongin-si (KR); Eunsil Han, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 19/077,514

(22) Filed: Mar. 12, 2025

(65) Prior Publication Data

US 2026/0034045 A1    Feb. 5, 2026

Related U.S. Application Data

(63) Continuation of application No. PCT/KR2024/019085, filed on Nov. 28, 2024.

(30) Foreign Application Priority Data

Jul. 31, 2024    (KR) ........................ 10-2024-0101975
Nov. 27, 2024    (KR) ........................ 10-2024-0172277

(51) Int. Cl.
*A61K 8/64*    (2006.01)
*A61Q 5/00*    (2006.01)

(52) U.S. Cl.
CPC ............... *A61K 8/64* (2013.01); *A61Q 5/002* (2013.01)

(58) Field of Classification Search
None
See application file for complete search history.

(56) References Cited

U.S. PATENT DOCUMENTS

| | | |
|---|---|---|
| 2012/0052034 A1 | 3/2012 | Azizova et al. |
| 2016/0271043 A1 | 9/2016 | Cavaco Paulo et al. |
| 2018/0002376 A1* | 1/2018 | Adir ...................... A61K 38/07 |

FOREIGN PATENT DOCUMENTS

| | | |
|---|---|---|
| JP | 2021-534103 A | 12/2021 |
| KR | 10-1633640 B1 | 6/2016 |
| KR | 10-2084765 B1 | 3/2020 |
| WO | 2012/153337 A2 | 11/2012 |
| WO | 2015/056216 A2 | 4/2015 |
| WO | 2020/031150 A1 | 2/2020 |

OTHER PUBLICATIONS

Korean Office Action for KR 10-2024-0101975 dated Oct. 16, 2024.
Korean Written Decision on Registration for KR 10-2024-0101975 dated Dec. 6, 2024.
Chinese Patent Office, Communication issued Oct. 25, 2025 in copending Application No. 202510691404.8, with English translation.
Cruz et al., "Peptide—protein interactions within human hair keratins", International Journal of Biological Macromolecules 101, 2017, 805-814.
European Patent Office, Communication issued Nov. 24, 2025 in Copending Applicaton No. EP 24 88 3563.

* cited by examiner

*Primary Examiner* — Nicole P Babson
(74) *Attorney, Agent, or Firm* — Sughrue Mion, PLLC

(57)    ABSTRACT

A composition for hair protection or hair strengthening is disclosed. The composition may include i) a peptide including one or more sequence units of Xaa-Yaa-Zaa (wherein the Xaa, Yaa, and Zaa are each selected from C (cysteine), K (lysine), W (tryptophan), V (valine), L (leucine), or F (phenylalanine), and wherein the Xaa, Yaa, and Zaa are all different, and wherein, when Xaa and Yaa are C and K, respectively, Zaa is not L); ii) a peptide derivative in which a fatty acid or an organic acid is bound to the N-terminus of the peptide; or iii) at least three amino acids selected from C, K, W, V, L, or F.

2 Claims, 10 Drawing Sheets

Specification includes a Sequence Listing.

FIG. 1

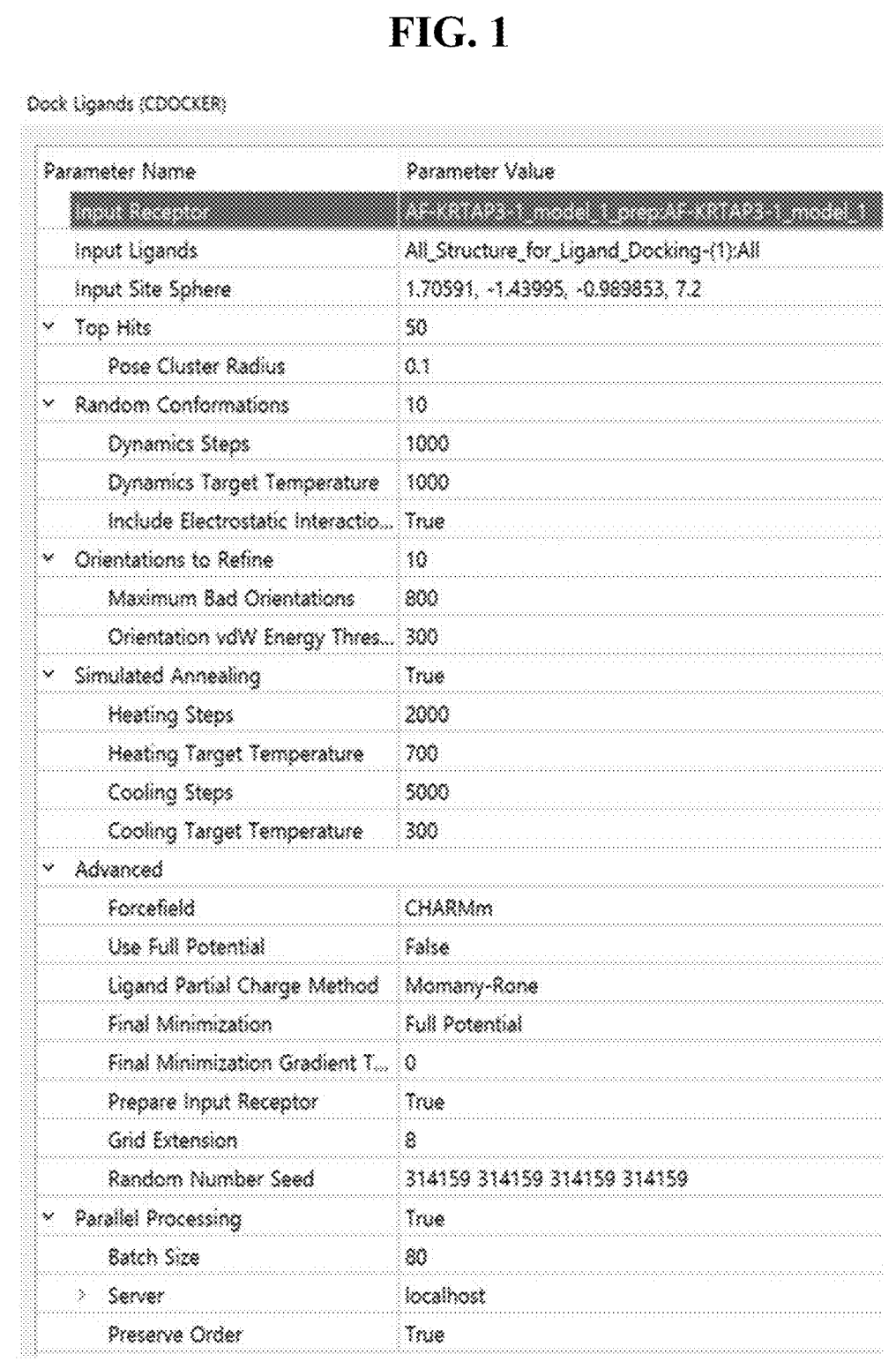

Dock Ligands (CDOCKER)

| Parameter Name | Parameter Value |
|---|---|
| Input Receptor | 1F_GTP_A_1_prod_1_prot_1F_GTP_A_1_prod_1 |
| Input Ligands | All_Structure_for_Ligand_Docking-(1):All |
| Input Site Sphere | 1.70591, -1.43995, -0.989853, 7.2 |
| ˅ Top Hits | 50 |
|     Pose Cluster Radius | 0.1 |
| ˅ Random Conformations | 10 |
|     Dynamics Steps | 1000 |
|     Dynamics Target Temperature | 1000 |
|     Include Electrostatic Interactio... | True |
| ˅ Orientations to Refine | 10 |
|     Maximum Bad Orientations | 800 |
|     Orientation vdW Energy Thres... | 300 |
| ˅ Simulated Annealing | True |
|     Heating Steps | 2000 |
|     Heating Target Temperature | 700 |
|     Cooling Steps | 5000 |
|     Cooling Target Temperature | 300 |
| ˅ Advanced | |
|     Forcefield | CHARMm |
|     Use Full Potential | False |
|     Ligand Partial Charge Method | Momany-Rone |
|     Final Minimization | Full Potential |
|     Final Minimization Gradient T... | 0 |
|     Prepare Input Receptor | True |
|     Grid Extension | 8 |
|     Random Number Seed | 314159 314159 314159 314159 |
| ˅ Parallel Processing | True |
|     Batch Size | 80 |
|   ˃ Server | localhost |
|     Preserve Order | True |

SEQUENCE LISTING

Sequence total quantity: 22
SEQ ID NO: 1          moltype = AA  length = 6
FEATURE               Location/Qualifiers -continued

```
source                    1..6
                          mol_type = protein
                          organism = synthetic construct
SEQUENCE: 1
CKFCKF                                                               6

SEQ ID NO: 2              moltype = AA   length = 9
FEATURE                   Location/Qualifiers
source                    1..9
                          mol_type = protein
                          organism = synthetic construct
SEQUENCE: 2
CKFCKFCKF                                                            9

SEQ ID NO: 3              moltype = AA   length = 12
FEATURE                   Location/Qualifiers
source                    1..12
                          mol_type = protein
                          organism = synthetic construct
SEQUENCE: 3
CKFCKFCKFC KF                                                        12

SEQ ID NO: 4              moltype = AA   length = 6
FEATURE                   Location/Qualifiers
source                    1..6
                          mol_type = protein
                          organism = synthetic construct
SEQUENCE: 4
CWKCWK                                                               6

SEQ ID NO: 5              moltype = AA   length = 9
FEATURE                   Location/Qualifiers
source                    1..9
                          mol_type = protein
                          organism = synthetic construct
SEQUENCE: 5
CWKCWKCWK                                                            9

SEQ ID NO: 6              moltype = AA   length = 12
FEATURE                   Location/Qualifiers
source                    1..12
                          mol_type = protein
                          organism = synthetic construct
SEQUENCE: 6
CWKCWKCWKC WK                                                        12

SEQ ID NO: 7              moltype = AA   length = 6
FEATURE                   Location/Qualifiers
source                    1..6
                          mol_type = protein
                          organism = synthetic construct
SEQUENCE: 7
KCVKCV                                                               6

SEQ ID NO: 8              moltype = AA   length = 9
FEATURE                   Location/Qualifiers
source                    1..9
                          mol_type = protein
                          organism = synthetic construct
SEQUENCE: 8
KCVKCVKCV                                                            9

SEQ ID NO: 9              moltype = AA   length = 12
FEATURE                   Location/Qualifiers
source                    1..12
                          mol_type = protein
                          organism = synthetic construct
SEQUENCE: 9
KCVKCVKCVK CV                                                        12

SEQ ID NO: 10             moltype = AA   length = 11
FEATURE                   Location/Qualifiers
source                    1..11
                          mol_type = protein
                          organism = synthetic construct
SEQUENCE: 10
CCQSSCCKPS C                                                         11

SEQ ID NO: 11             moltype = AA   length = 11
```

-continued

```
FEATURE              Location/Qualifiers
source               1..11
                     mol_type = protein
                     organism = synthetic construct
SEQUENCE: 11
CVSSCCKPQC C                                                              11

SEQ ID NO: 12        moltype = AA  length = 10
FEATURE              Location/Qualifiers
source               1..10
                     mol_type = protein
                     organism = synthetic construct
SEQUENCE: 12
PIYCRRTCYH                                                               10

SEQ ID NO: 13        moltype = AA  length = 10
FEATURE              Location/Qualifiers
source               1..10
                     mol_type = protein
                     organism = synthetic construct
SEQUENCE: 13
DCKLPCNPCA                                                               10

SEQ ID NO: 14        moltype = AA  length = 10
FEATURE              Location/Qualifiers
source               1..10
                     mol_type = protein
                     organism = synthetic construct
SEQUENCE: 14
CLPCLPAASC                                                               10

SEQ ID NO: 15        moltype = AA  length = 10
FEATURE              Location/Qualifiers
source               1..10
                     mol_type = protein
                     organism = synthetic construct
SEQUENCE: 15
CEPAICEPSC                                                               10

SEQ ID NO: 16        moltype = AA  length = 11
FEATURE              Location/Qualifiers
source               1..11
                     mol_type = protein
                     organism = synthetic construct
SEQUENCE: 16
CQCSCCKPYC S                                                             11

SEQ ID NO: 17        moltype = AA  length = 13
FEATURE              Location/Qualifiers
source               1..13
                     mol_type = protein
                     organism = synthetic construct
SEQUENCE: 17
GGVCGPSPPC ITT                                                           13

SEQ ID NO: 18        moltype = AA  length = 15
FEATURE              Location/Qualifiers
source               1..15
                     mol_type = protein
                     organism = synthetic construct
SEQUENCE: 18
CWKCWKKCLK CLKCV                                                         15

SEQ ID NO: 19        moltype = AA  length = 15
FEATURE              Location/Qualifiers
source               1..15
                     mol_type = protein
                     organism = synthetic construct
SEQUENCE: 19
CKWCWKKCLK CVKCL                                                         15

SEQ ID NO: 20        moltype = AA  length = 15
FEATURE              Location/Qualifiers
source               1..15
                     mol_type = protein
                     organism = synthetic construct
SEQUENCE: 20
CKWKCFCKFC WKKCV                                                         15
```

-continued

```
SEQ ID NO: 21        moltype = AA   length = 15
FEATURE              Location/Qualifiers
source               1..15
                     mol_type = protein
                     organism = synthetic construct
SEQUENCE: 21
KCFKCFCKWC KFKCV                                             15

SEQ ID NO: 22        moltype = AA   length = 15
FEATURE              Location/Qualifiers
source               1..15
                     mol_type = protein
                     organism = synthetic construct
SEQUENCE: 22
CKFCKWKCFK CVKCF                                             15
```

COMPOSITION FOR HAIR PROTECTION OR HAIR STRENGTHENING

CROSS REFERENCE TO RELATED APPLICATION

This application is a continuation application of International Application No. PCT/KR2024/019085 filed on Nov. 28, 2024 which claims the benefit of priority from Korean Patent Application No. 10-2024-0101975, filed on Jul. 31, 2024 and Korean Patent Application No. 10-2024-0172277, filed on Nov. 27, 2024, the entire contents of which is incorporated herein for all purposes by this reference.

INCORPORATION BY REFERENCE OF SEQUENCE LISTING

The instant application contains a Sequence Listing which has been filed electronically in xml format and is hereby incorporated by reference in its entirety. Said xml copy, created on Mar. 3, 2025, is named Q306974_Sequence Listing.xml and is 19.6 KB in size.

BACKGROUND OF THE INVENTION

Field of the Invention

The present disclosure relates to a composition for hair protection or hair strengthening and the corresponding use of said composition.

Description of the Related Art

Chemical treatments for hair, such as perms and dyeing, are increasing for cosmetic purposes, which causes nonspecific damage to various structural proteins or lipid components that make up the hair. Since eyebrows and eyelashes are shorter, thinner, and fewer in number than hair in other areas (e.g., capillus), they are more vulnerable to physical and chemical stimuli than hair in other areas (e.g., capillus), and if damaged, the cosmetic loss is significant.

Hair (e.g., capillus, eyebrows, eyelashes) is largely composed of the hair cuticle, hair cortex, cell membrane complex (CMC), and hair medulla. Physical stimuli mainly cause damage to the hair cuticle, and chemical stimuli mainly cause loss of CMC and hair cortex. Repeated exposure to these stimuli can irreversibly change the hair (e.g., capillus, eyebrows, eyelashes), resulting in damage, breakage, and/or loss of hair (e.g., capillus, eyebrows, eyelashes), or changing the hair to a weak state that does not form the desired cosmetic appearance of the individual. In order to restore the tensile strength of hair to the level before damage, there is a method of filling the gap between the lost CMC and hair cortex with a predetermined component and combining it with the predetermined component to increase the structural strength of the hair. On the other hand, it is not easy to restore the CMC composed of the lipid layer using a conventional hair composition containing an organic acid, etc.

SUMMARY OF THE INVENTION

Technical Problem

One aspect of the present disclosure is directed to providing a peptide or peptide derivative which is composed of a substance existing in the human body, has a significantly low risk of irritation, and at the same time, supplements damaged components in the hair (e.g., capillus, eyebrows, eyelashes) to enhance the strength and elasticity of the hair (e.g., capillus, eyebrows, eyelashes).

One aspect of the present disclosure is directed to providing a peptide that exhibits a hair protection effect, a damaged hair repair effect, or a hair strengthening effect.

One aspect of the present disclosure is directed to providing a peptide derivative that exhibits a hair protection effect, a damaged hair repair effect, or a hair strengthening effect.

One aspect of the present disclosure is directed to providing a composition for hair protection, damaged hair repair, or hair strengthening.

Technical Solution

A peptide according to one aspect of the present disclosure is a peptide comprising one or more sequence units of Xaa-Yaa-Zaa: wherein the Xaa, Yaa, and Zaa are each independently selected from the group consisting of C (Cys; cysteine), K (Lys; lysine), W (Trp; tryptophan), V (Val; valine), L (Leu; leucine) and F (Phe; phenylalanine), and wherein the Xaa, Yaa, and Zaa are all different and wherein, when Xaa and Yaa are C and K, respectively, Zaa is not L.

A peptide derivative according to one aspect of the present disclosure is one in which a fatty acid or an organic acid is bound to the N-terminus of the peptide.

A composition for hair protection, damaged hair repair, or hair strengthening according to one aspect of the present disclosure comprises the peptide as defined above.

A composition for hair protection, damaged hair repair, or hair strengthening according to one aspect of the present disclosure comprises the peptide derivative as defined above.

A composition for hair protection, damaged hair repair, or hair strengthening according to one aspect of the present disclosure comprises a mixture of at least three amino acids selected from the group consisting of C, K, W, V. L (Leu; leucine) and F.

Advantageous Effects of Invention

The peptide, peptide derivative, and/or composition according to one aspect of the present disclosure can improve the strength (or rigidity) and/or elasticity of hair (e.g., damaged hair). The peptide, peptide derivative, and/or composition according to one aspect of the present disclosure can bind to the hair cuticle layer, the cortex and/or the CMC of hair (e.g., damaged hair) to improve the strength of the hair, for example the tensile strength of the hair.

The peptide, peptide derivative, and/or composition according to one aspect of the present disclosure can repair damage of the CMC structure in damaged hair, and ultimately repair the hair, for example improve the rigidity, smoothness, and/or elasticity of damaged hair.

BRIEF DESCRIPTION OF THE DRAWINGS

FIG. 1 shows the conditions for calculating the binding energy of keratin protein and a three-dimensional peptide molecule file using the CDocker module of Discovery Studio software (DASSAULT Systems).

US 12,594,228 B2

3

Figure 3:
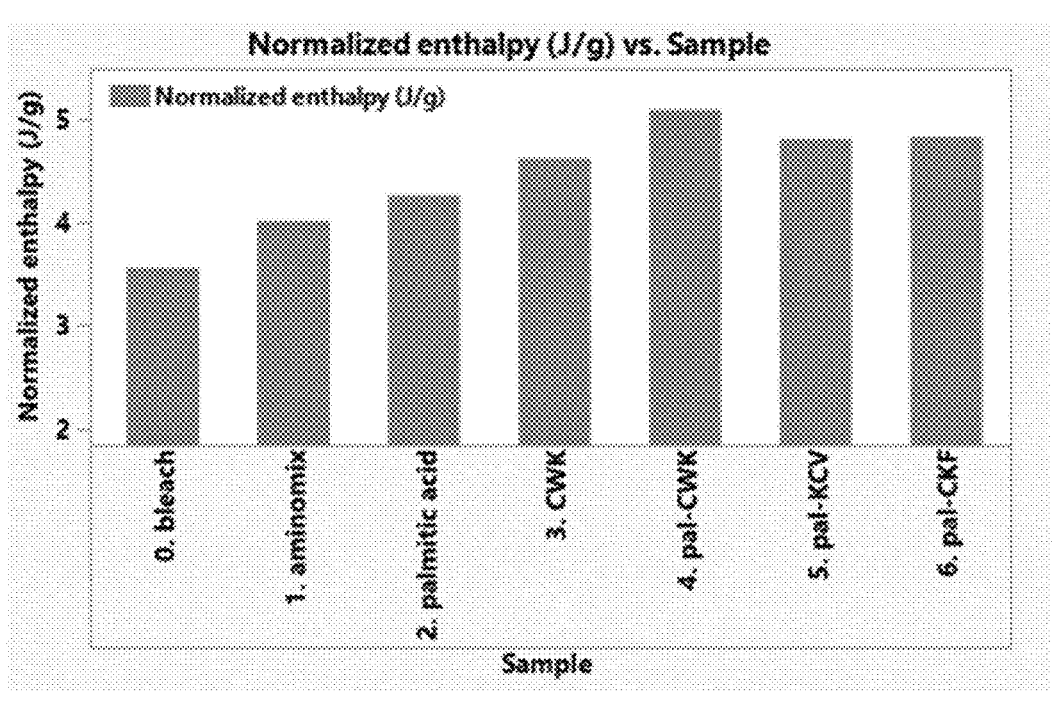

FIG. 3 shows the change in denaturation enthalpy of hair by treatment with an amino acid mixture, a tripeptide, and a tripeptide having a fatty acid bound to the N-terminus.

Figure 4:
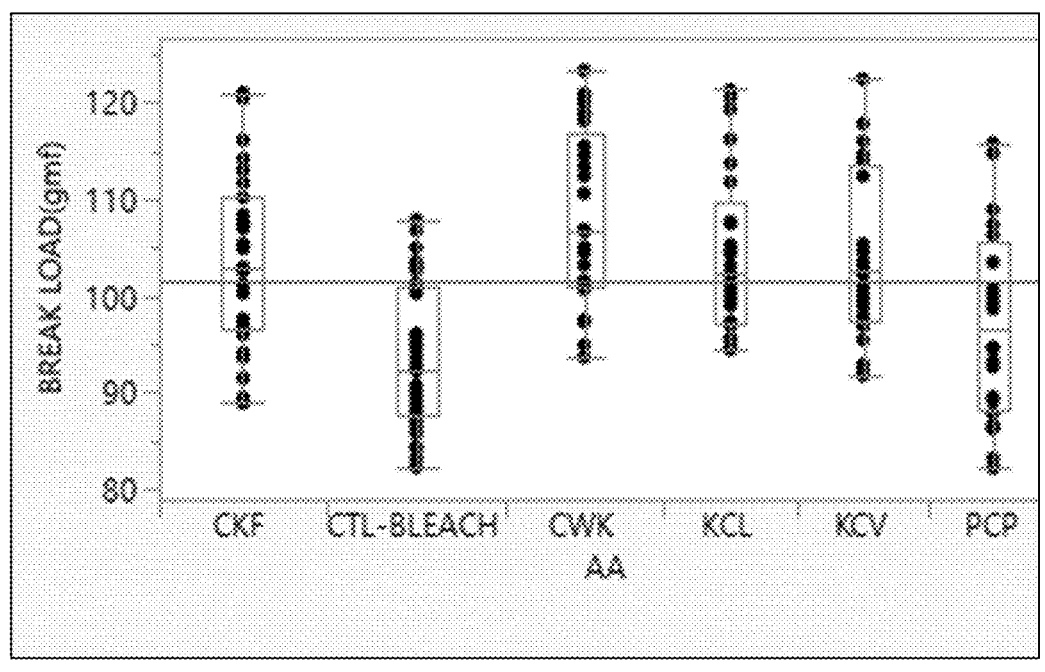

FIG. 4 shows the change in tensile strength of hair by treatment with a tripeptide.

Figure 5:
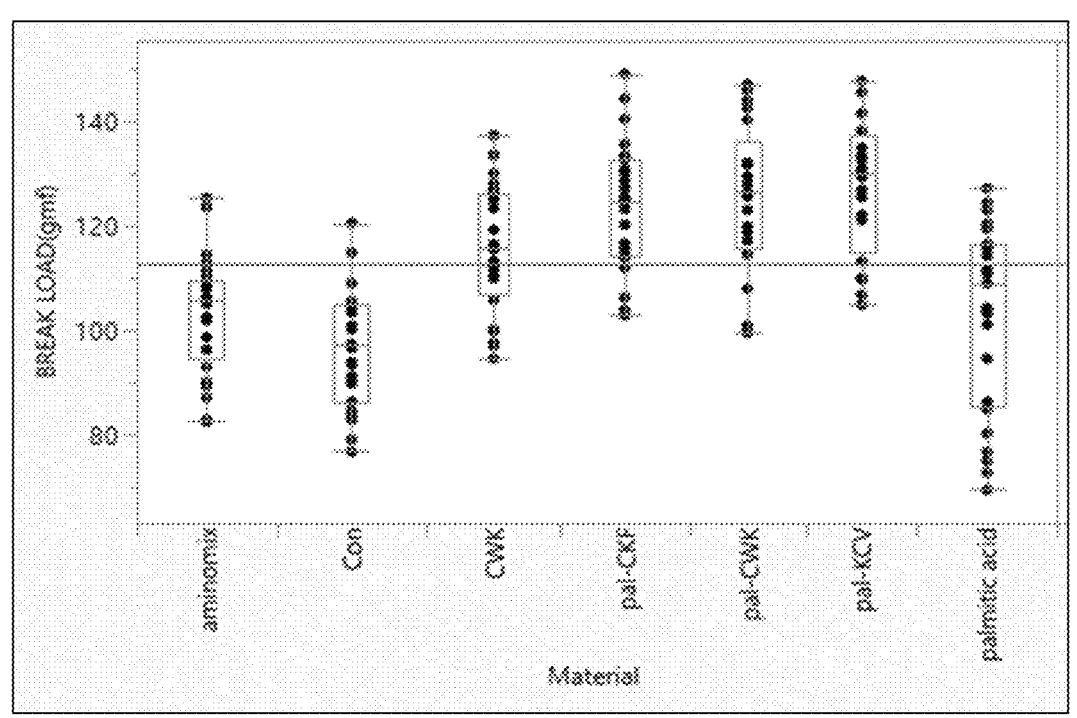

FIG. 5 shows the change in tensile strength of hair by treatment with a tripeptide having a fatty acid bound to the N-terminus, an amino acid mixture, and a tripeptide.

Figure 6:
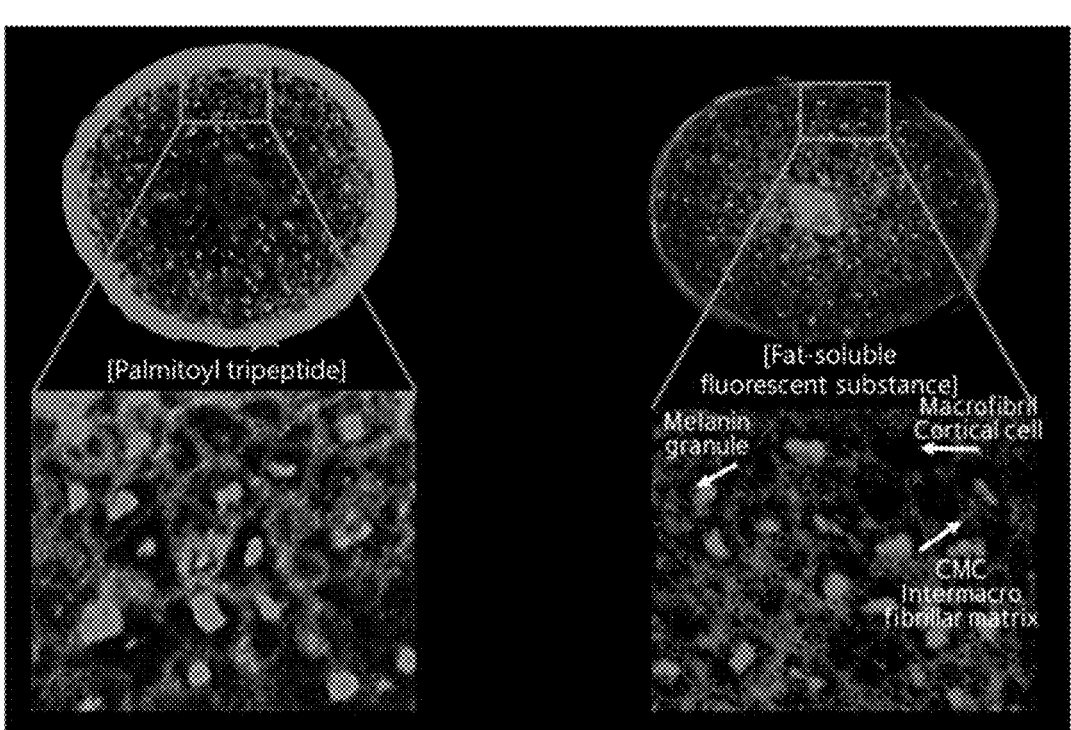

FIG. 6 is a confocal microscopic photograph showing the form in which fluorescently labeled palmitoyl tripeptide (a tripeptide having a fatty acid bound to the N-terminus; left photo) and a fat-soluble fluorescent substance (right photo) penetrates and binds to hair.

Figure 7:
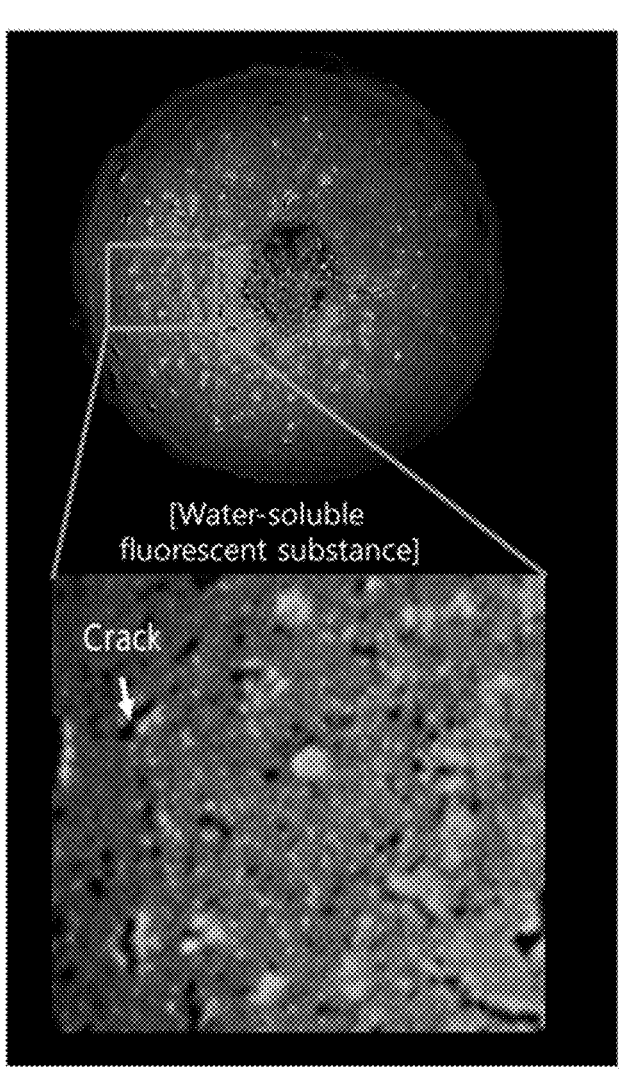

FIG. 7 is a confocal microscopic photograph showing the form in which a water-soluble fluorescent substance penetrates and binds to hair.

Figure 8:
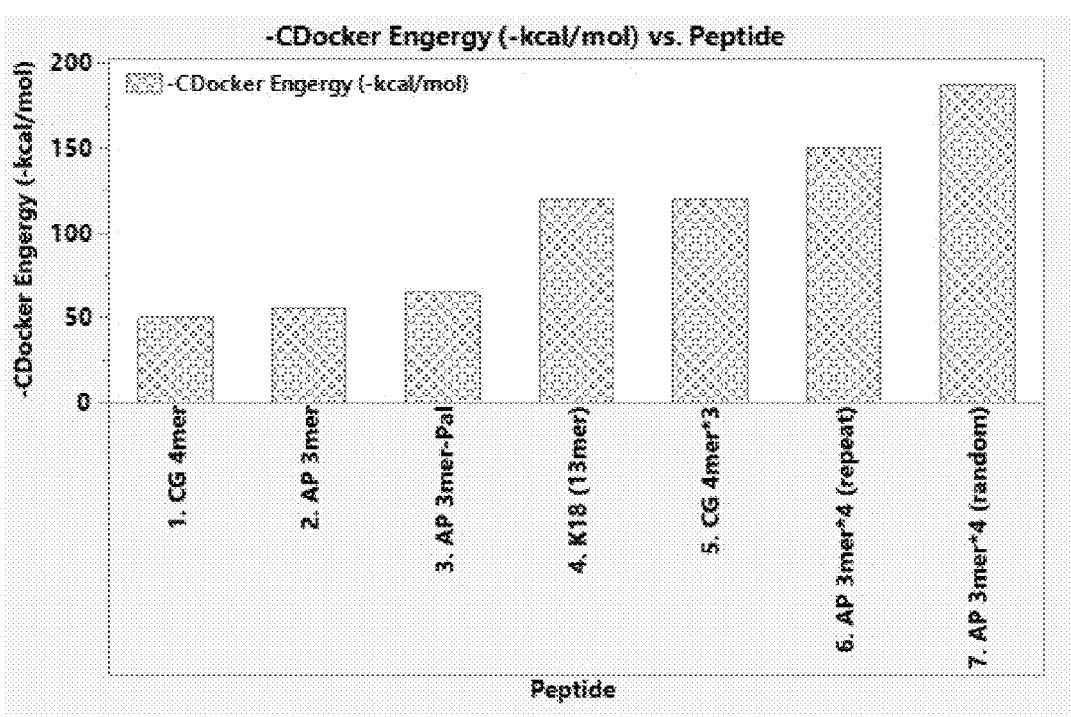

FIG. 8 is a result showing the binding strength of an oligopeptide that repeats or combines a tripeptide sequence to hair.

Figure 9:
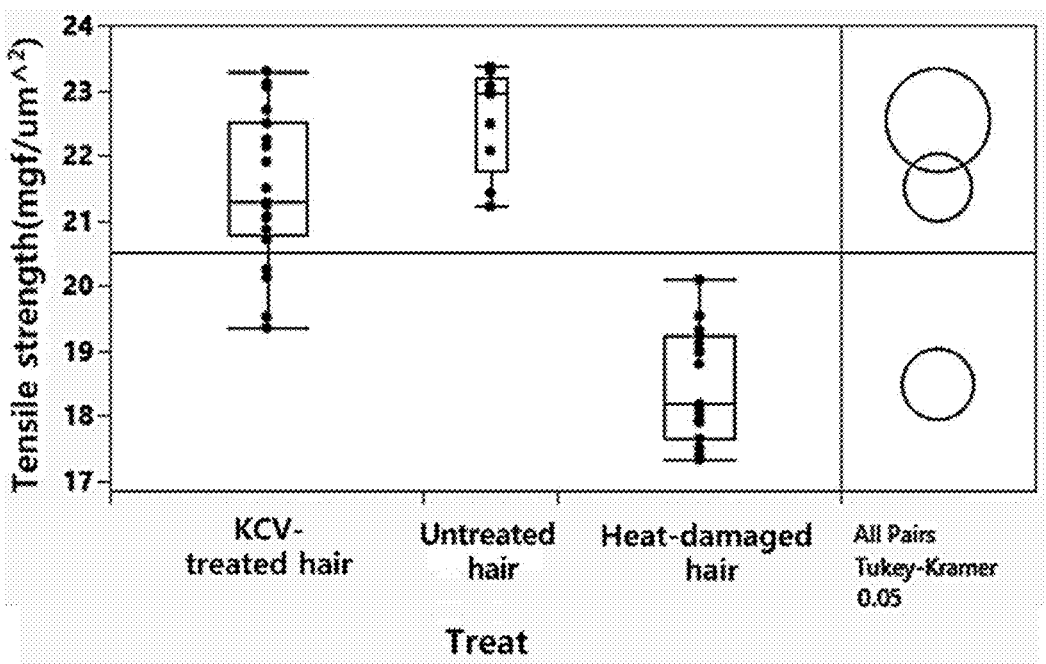

FIG. 9 shows the change in tensile strength of eyebrows by treatment with a tripeptide and a tripeptide having a fatty acid bound to the N-terminus.

Figure 10:
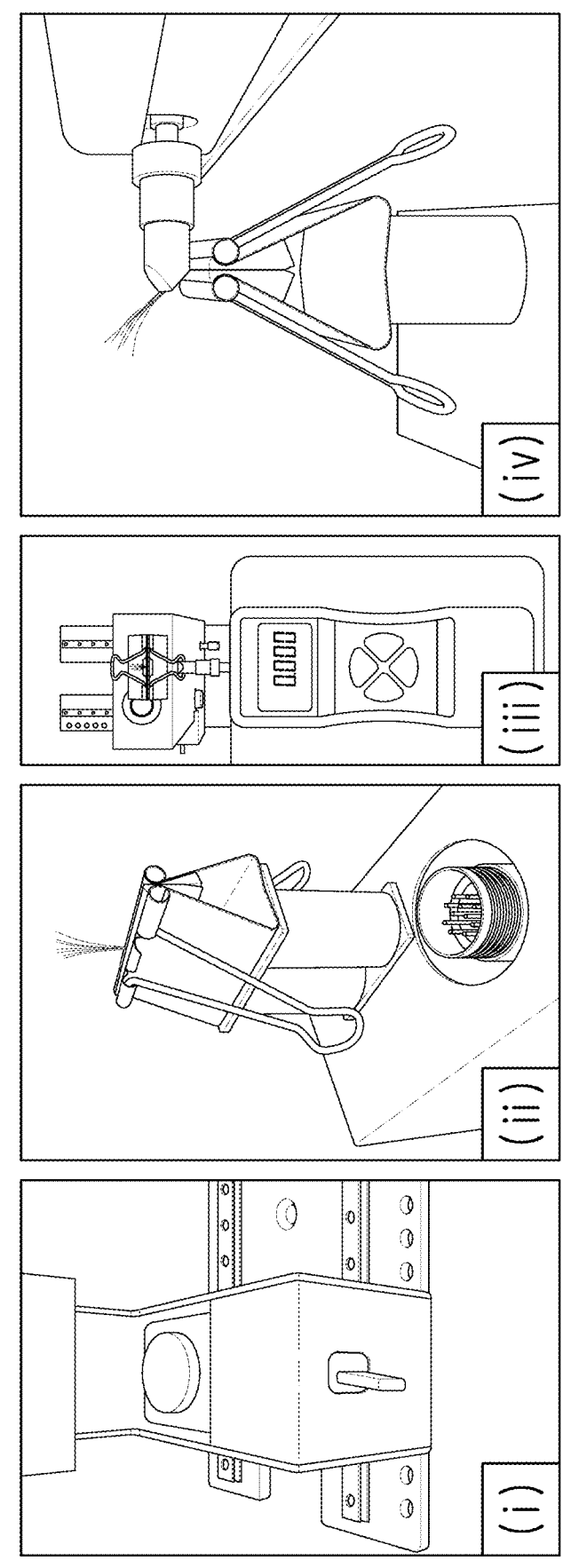

FIG. 10 shows a step-by-step method for measuring eyebrow elasticity.

Figure 11:
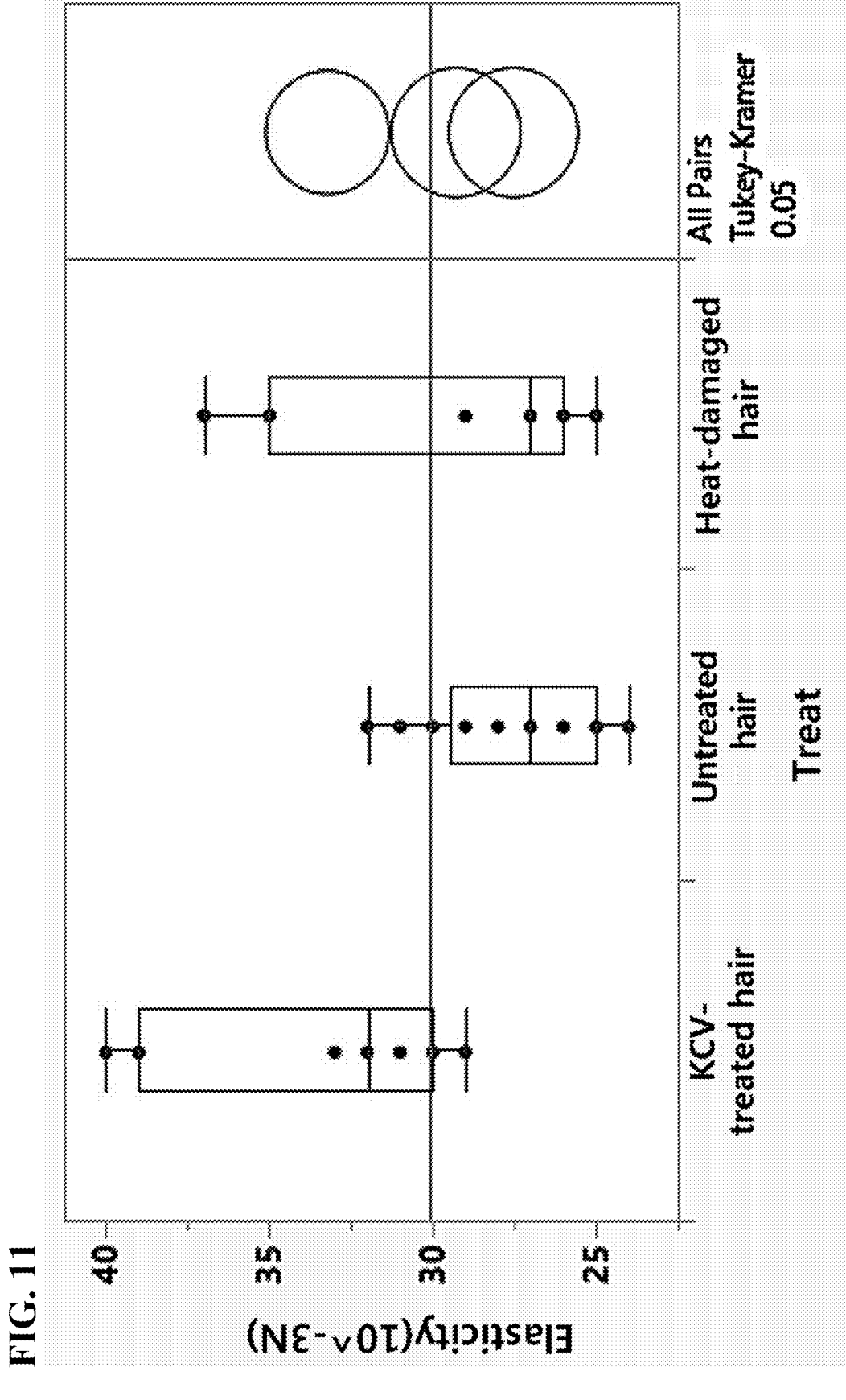

FIG. 11 shows the elasticity of hair by treatment with a tripeptide and a tripeptide having a fatty acid bound to the N-terminus.

DETAILED DESCRIPTION OF THE INVENTION

The various embodiments of this document and the terms used herein are not intended to limit the technical features described in this document to specific embodiments, but should be understood to include various modifications, equivalents, or substitutes of the embodiments.

The present inventors have developed a material that can bind to the hair cuticle layer, the CMC (interstitial material) and/or the cortex of damaged hair (e.g., capillus, eyebrows, eyelashes) to fill the gap, increase the structural strength of the hair, and/or exhibit a hair (e.g., capillus, eyebrows, eyelashes) damage repair effect.

In one embodiment, the present inventors selected a peptide comprising an amino acid sequence having excellent binding affinity to structural proteins (KRT 33B, KRT 85, KAP 3-1) found in damaged hair. Based on the amino acid sequence which shows a high ranking among the selected peptide sequences, i) a tripeptide and ii) a tripeptide having a fatty acid covalently bound to the N-terminus, etc. were synthesized, and it was confirmed that they increased the structural strength of the hair (e.g., capillus, eyebrows, eyelashes), such as the tensile strength of the hair (e.g., capillus, eyebrows, eyelashes). In addition, iii) a mixture was prepared by combining amino acids constituting a tripeptide sequence corresponding to the high ranking among the selected peptide sequences, and it was confirmed that the amino acid mixture increased the structural strength of the hair (e.g., capillus, eyebrows, eyelashes), such as the tensile strength of hair (e.g., capillus, eyebrows, eyelashes).

Definition of Terms

In this disclosure, Xaa, Yaa, Zaa each represent an amino acid.

In this disclosure, C or Cys represents cysteine, K or Lys represents lysine, W or Trp represents tryptophan, V or Val represents valine, L or Leu represents leucine, and F or Phe represents phenylalanine.

In this disclosure, the amino acid sequence of a peptide is written from the left in the order of N-terminus to C-terminus. On the other hand, the direction of synthesis in which the peptide is synthesized, starts from the C-terminus to the N-terminus, which is opposite to the direction of reading the peptide sequence. The direction of writing/reading the peptide sequence and the direction of synthesis of the peptide sequence are well known in the art.

In this disclosure, the term "hair strengthening" usually involves increasing the strength of hair, and preferably includes, for example, increasing the tensile strength of hair and/or increasing the denaturation enthalpy of hair. In this disclosure, hair strengthening may involve increasing the strength of undamaged hair or damaged hair. Damaged hair may be caused by heat or chemical treatments (e.g., dyeing, perming, bleaching). Damaged hair may be caused by heat or chemical treatments (e.g., dyeing, perming, bleaching) that have damaged the main structural components of the hair. In one embodiment, a composition for hair strengthening may be a composition for increasing the strength and/or elasticity of hair.

In the present disclosure, the term "hair protection" usually involves, but is not limited to, inhibiting damage to hair. In the present disclosure, hair protection preferably includes, but is not limited to, preventing undamaged hair from being damaged; or preventing damaged hair from being further damaged.

In the present disclosure, the term "hair" means all types of hair on an individual (e.g., including a mammal). For example, hair in the present disclosure may include, but is not limited to, at least one selected from the group consisting of capillus (head hair), eyebrows, eyelashes, and body hair (e.g., chest hair, leg hair). The structure and composition of other types of hair (e.g., eyebrows, eyelashes) present in different parts of the scalp are not significantly different from those of the scalp (Qianqian Su, Cheng Zhou, Congfen He, Qian Jiao, Zidi Wang, Yan Jia Research Progress in Composition, Classification and Influencing Factors of Hair. *Asian J Beauty Cosmetol* 2023; 21 (3). 503-516). In addition, although the size and shape of hair follicles in the body are different, their basic structure is the same (Jennifer V. Nguyen M D. The Biology, Structure, and Function of Eyebrow Hair. *J Drugs Dermatol.* 2014; 13 (suppl 1): s12-s16). Therefore, it can be said that the effect of peptides or peptide derivatives on capillus is substantially the same in hair in other parts of the body (e.g., eyebrows and/or eyelashes).

In the present disclosure, the term "fatty acid of C8 to C30" means a fatty acid having 8 to 30 carbon atoms. In the present disclosure, the term "fatty acid of Cn1 (integer) to Cn2 (integer)" means a fatty acid having n1 (integer) to n2 (integer) carbon atoms. According to the present invention, the term "fatty acid" includes a saturated or unsaturated fatty acid.

In the present disclosure, the term "peptide derivative" means a peptide in which one or more amino acid(s) of the above-defined parent peptide is/are chemically modified or a peptide in which the above-defined parent peptide is modified by adding an amino acid. For example, in the present disclosure, the peptide derivative may be a peptide as defined above in which any component (e.g., a compound, a fatty acid, an organic acid, etc., for example a C1 to C30 fatty acid, preferably a C15 to C20 fatty acid) is bound to the N-terminus or C-terminus of the parent peptide.

Peptide or Peptide Derivative Exhibiting Hair Protection Effect, Damaged Hair Repair Effect or Hair Strengthening Effect One aspect of the present disclosure provides a peptide comprising one or more sequence units of Xaa-Yaa-Zaa:

wherein the Xaa, Yaa, and Zaa are each independently selected from the group consisting of C (cysteine), K (lysine), W (tryptophan), V (valine), L (leucine) and F (phenylalanine), and wherein the Xaa, Yaa, and Zaa are all different and wherein, when Xaa and Yaa are C and K, respectively, Zaa is not L.

In one embodiment, two of Xaa, Yaa and Zaa may be C and K, respectively, wherein, when Xaa and Yaa are C and K, respectively, Zaa is not L.

In one embodiment, two of Xaa, Yaa and Zaa may be C and K, respectively, and the remaining one may be selected from the group consisting of W, V, and F.

In one embodiment, the peptide may be a tripeptide consisting of one sequence unit of Xaa-Yaa-Zaa.

In one embodiment, the peptide is a tripeptide selected from the group consisting of CKF, CWK, or KCV.

In one embodiment, the peptide may be an oligopeptide consisting of a plurality of the sequence units of Xaa-Yaa-Zaa. In this case, the plurality of sequence units of Xaa-Yaa-Zaa combined may be all identical, partially identical, or not identical.

In one embodiment, the peptide may be an oligopeptide consisting of 2 to 10 of the sequence units of Xaa-Yaa-Zaa but is not limited thereto. For example, the peptide may be an oligopeptide consisting of 2, 3, 4, 5, 6, 7, 8, 9, or 10 of the sequence units of Xaa-Yaa-Zaa but is not limited thereto.

In one embodiment, the peptide may be an oligopeptide consisting of 2 to 5, preferably 2 to 4 of the sequence units of Xaa-Yaa-Zaa.

In one embodiment, the oligopeptide may be a peptide in which 3 to 30 amino acids are bound, but is not limited thereto. For example, an oligopeptide may a peptide in which 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 3 or less, 4 or less, 5 or less, 6 or less, 7 or less, 8 or less, 9 or less, 10 or less, 11 or less, 12 or less, 13 or less, 14 or less, 15 or less, 16 or less, 17 or less, 18 or less, 19 or less, 20 or less, 21 or less, 22 or less, 23 or less, 24 or less, 25 or less, 26 or less, 27 or less, 28 or less, 29 or less, 30 or less amino acids, or amino acids in their combined range (e.g., 3 to 24, 3 to 15, 3 to 12) are bound.

In one embodiment, the peptide is an oligopeptide composed of 2 to 5, preferably 2 to 4 of the sequence units of Xaa-Yaa-Zaa, and the sequence units constituting the oligopeptide may be all identical, partially identical, or not all identical.

In one embodiment, the peptide is an oligopeptide composed of 2 to 5, preferably 2 to 4 of the sequence units of Xaa-Yaa-Zaa, and the sequence units constituting the oligopeptide may be all identical. In one embodiment, the peptide is an oligopeptide composed of 2 to 5, preferably 2 to 4 of the sequence units of Xaa-Yaa-Zaa, and at least one of the sequence units constituting the oligopeptide may be the same. In one embodiment, the peptide is an oligopeptide composed of 2 to 5, preferably 2 to 4 of the sequence units of Xaa-Yaa-Zaa, and some of the sequence units constituting the oligopeptide may be the same. In one embodiment, the peptide is an oligopeptide composed of 2 to 5, preferably 2 to 4 of the sequence units of Xaa-Yaa-Zaa, and not all of the sequence units constituting the oligopeptide may be the same.

In one embodiment, the peptide is an oligopeptide the amino acid sequence of which is CKFCKF (SEQ ID NO: 1), CKFCKFCKF (SEQ ID NO. 2), CKFCKFCKFCKF (SEQ ID NO: 3), CWKCWK (SEQ ID NO: 4), CWKCWKCWK (SEQ ID NO: 5), CWKCWKCWKCWK (SEQ ID NO: 6), KCVKCV (SEQ ID NO. 7), KCVKCVKCV (SEQ ID NO: 8), KCVKCVKCVKCV (SEQ ID NO: 9), CWKCWKKCLKCLKCV (SEQ ID NO: 18), CKWCWKKCLKCVKCL (SEQ ID NO: 19), CKWKCFCKFCWKKCV (SEQ ID NO: 20), KCFKCFCK-WCKFKCV (SEQ ID NO: 21), or CKFCKWKCFKCVKCF (SEQ ID NO: 22).

A peptide (e.g., tripeptide or oligopeptide) that exhibits a hair protection effect, a damaged hair repair effect, or a hair strengthening effect according to an embodiment of the present invention, particularly a tripeptide, is easy to synthesize due to its short sequence length and furthermore provides time and cost advantages.

In addition, one aspect of the present disclosure provides a peptide derivative having a fatty acid or organic acid bound to the N-terminus of the above-described peptides or oligopeptides.

In the present disclosure, the peptide derivative having a fatty acid or organic acid bound to the N-terminus may be one in which the N-terminus of the peptide is acylated. The acylation of the peptide N-terminus may be derived from a fatty acid or organic acid. In the present disclosure, the peptide derivative having a fatty acid or organic acid bound to the N-terminus may be an acyl derivative in which the N-terminus of the peptide is acylated.

In the present disclosure, the term "a fatty acid or organic acid is bound to the N-terminus of a peptide (or oligopeptide)" may mean that an acyl group derived from a fatty acid or organic acid is bound to the N-terminus of the peptide (or oligopeptide).

For example, the term "a fatty acid is bound to the N-terminus of the peptide (or oligopeptide)" may mean that an acyl group derived from a fatty acid is bound to the N-terminus of the peptide (or oligopeptide). For example, the term "an organic acid is bound to the N-terminus of the peptide (or oligopeptide)" may mean that an acyl group derived from an organic acid is bound to the N-terminus of the peptide (or oligopeptide).

That is, one aspect of the present disclosure provides a peptide derivative having a fatty acid or organic acid bound to the N-terminus of a peptide comprising one or more sequence units consisting of Xaa-Yaa-Zaa: wherein the Xaa, Yaa and Zaa are each independently selected from the group consisting of C, K, W, V. L and F. and wherein the Xaa, Yaa and Zaa are all different. In this case, when Xaa and Yaa are C and K, respectively, Zaa is not L. In this case, if Xaa and Yaa are C and K, respectively, Zaa may not be L.

As for Xaa, Yaa, Zaa, sequence units, and peptides, they are the same as described above, so a detailed description is omitted.

The "binding" of a fatty acid or organic acid to the N-terminus may be a covalent bond.

In one embodiment, the fatty acid may be a C2 to C80 fatty acid.

In one embodiment, the fatty acid may be, but is not limited to, a C8 to C30 fatty acid. For example, the fatty acid may be, but is not limited to, a C8 fatty acid, a C9 fatty acid, a C10 fatty acid, a C11 fatty acid, a C12 fatty acid, a C13 fatty acid, a C14 fatty acid, a C15 fatty acid, a C16 fatty acid, a C17 fatty acid, a C18 fatty acid, a C19 fatty acid, a C20 fatty acid, a C21 fatty acid, a C22 fatty acid, a C23 fatty acid, a C24 fatty acid, a C25 fatty acid, a C26 fatty acid, a C27 fatty acid, a C28 fatty acid, a C29 fatty acid, or a C30 fatty acid. For example, the fatty acid may be, but is not limited to, a C8 to C30 fatty acid, a C9 to C29 fatty acid, a C9 to C28 fatty acid, a C9 to C27 fatty acid, a C9 to C26 fatty acid, a C9 to C25 fatty acid, a C9 to C24 fatty acid, a C10 to C24 fatty acid, a C9 to C23 fatty acid, a C10 to C22 fatty acid, a C11 to C21 fatty acid, a C12 to C20 fatty acid, a C13 to C19 fatty acid, a C14 to C18 fatty acid, a C15 to C20 fatty acid, or a C15 to C17 fatty acid. In one preferred embodiment the fatty acid may be a C15 to C20 fatty acid, preferably a C15 to C17 fatty acid.

In one embodiment, the acyl group derived from the fatty acid may be, but is not limited to, an acyl group derived from a C8 to C30 fatty acid. For example, the acyl group derived from the fatty acid may be, but is not limited to, an acyl group derived from a C8 fatty acid, a C9 fatty acid, a C10 fatty acid, a C11 fatty acid, a C12 fatty acid, a C13 fatty acid, a C14 fatty acid, a C15 fatty acid, a C16 fatty acid, a C17 fatty acid, a C18 fatty acid, a C19 fatty acid, a C20 fatty acid, a C21 fatty acid, a C22 fatty acid, a C23 fatty acid, a C24 fatty acid, a C25 fatty acid, a C26 fatty acid, a C27 fatty acid, a C28 fatty acid, a C29 fatty acid, or a C30 fatty acid. For example, the acyl group derived from the fatty acid may be an acyl group derived from a C8 to C30 fatty acid, a C9 to C29 fatty acid, a C9 to C28 fatty acid, a C9 to C27 fatty acid, a C9 to C26 fatty acid, a C9 to C25 fatty acid, a C9 to C24 fatty acid, a C10 to C24 fatty acid, a C9 to C23 fatty acid, a C10 to C22 fatty acid, a C11 to C21 fatty acid, a C12 to C20 fatty acid, a C13 to C19 fatty acid, a C14 to C18 fatty acid, a C15 to C20 fatty acid or a C15 to C17 fatty acid, but is not limited thereto. In a preferred embodiment, the acyl group derived from the fatty acid may be an acyl group derived from a C15 to C20 fatty acid, preferably an acyl group derived from a C15 to C17 fatty acid.

In general, according to the present invention the fatty acid may be a saturated or unsaturated fatty acid.

In general, according to the present invention, the acyl group derived from the fatty acid may be saturated or unsaturated.

In one embodiment, the fatty acid may be unsubstituted or substituted. For example, the fatty acid may be unsubstituted or substituted with at least one substituent selected from the group consisting of alkyl, alkoxy, aryl, hydroxy, amino, acyl amino, sulfate and sulfide, but is not limited thereto, preferably with at least one substituent selected from the group consisting of alkyl, alkoxy, hydroxy and amino.

In one embodiment, the acyl group derived from the fatty acid may be unsubstituted or substituted. For example, the acyl group derived from the fatty acid may be unsubstituted or substituted with at least one substituent selected from the group consisting of alkyl, alkoxy, aryl, hydroxy, amino, acyl amino, sulfate, and sulfide, but is not limited thereto, and preferably, may be substituted with at least one substituent selected from the group consisting of alkyl, alkoxy, hydroxy, and amino.

In one embodiment, the fatty acid may be at least one selected from the group consisting of caprylic acid (C8:0), capric acid (C10:0), lauric acid (C12:0), myristic acid (C14.0), palmitic acid (C16:0), stearic acid (C18:0), arachidic acid (C20:0), behenic acid (C22:0), lignoceric acid (C24:0), cerotic acid (C26:0), myristoleic acid (C14:1), palmitoleic acid (C16.1), oleic acid (C18:1), and eicosenoic acid (C20:1) but is not limited thereto. In one preferred embodiment, the fatty acid may be at least one selected from the group consisting of palmitic acid, stearic acid and arachidic acid. In one preferred embodiment, the fatty acid may be at least one selected from the group consisting of palmitoleic acid, oleic acid and eicosenoic acid.

In one embodiment, the acyl group derived from the fatty acid may be at least one selected from the group consisting of capryloyl group (C8:0), decanoyl group (C10:0), lauroyl group (C12:0), myristoyl group (C14:0), palmitoyl group (C16:0), stearoyl group (C18:0), arachidoyl group (C20:0), behenoyl group (C22:0), lignoceroyl group (C24:0), cerotoyl group (C26:0), myristoleoyl group (C14:1), palmitoleoyl group (C16:1), oleoyl group (C18:1), and eicosenooyl group (C20:1), but is not limited thereto. In one preferred embodiment, the acyl group derived from the fatty acid may be at least one selected from the group consisting of palmitoyl group, stearoyl group, and arachidoyl group. In one preferred embodiment, the fatty acid may be at least one selected from the group consisting of palmitoleoyl group, oleoyl group, and eicosenooyl group.

In one embodiment, the organic acid may be a saturated or unsaturated organic acid.

In general, according to the present invention, the acyl group derived from the organic acid may be saturated or unsaturated.

According to the present invention, the organic acid may be unsubstituted or substituted. For example, the organic acid may be unsubstituted or substituted with at least one substituent selected from the group consisting of alkyl, alkoxy, aryl, hydroxy, amino, acyl amino, sulfate, and sulfide, but is not limited thereto, preferably with at least one substituent selected from the group consisting of alkyl, alkoxy, hydroxy and amino.

According to the present invention, the acyl group derived from the organic acid may be unsubstituted or substituted. For example, the acyl group derived from the organic acid may be unsubstituted or substituted with at least one substituent selected from the group consisting of alkyl, alkoxy, aryl, hydroxy, amino, acyl amino, sulfate, and sulfide, but is not limited thereto, and preferably, may be substituted with at least one substituent selected from the group consisting of alkyl, alkoxy, hydroxy, and amino.

In one embodiment, the organic acid may be at least one selected from the group consisting of acetic acid, citric acid, formic acid, trifluoroacetic acid, succinic acid, gallic acid, and lactic acid, but is not limited thereto.

In one embodiment, the acyl group derived from the organic acid may be at least one selected from the group consisting of an acetyl group, a citryl group, a formyl group, a trifluoroacetyl group, a succinyl group, a galloyl group, and a lactyl group, but is not limited thereto.

In one embodiment, the peptide derivative may be a tripeptide consisting of one sequence unit of Xaa-Yaa-Zaa, wherein the N-terminus of the tripeptide is bound to a fatty acid or an organic acid. In one embodiment, the peptide derivative may be a tripeptide consisting of one sequence unit of Xaa-Yaa-Zaa, wherein the N-terminus of the tripeptide is bound to an acyl group derived from a fatty acid or an organic acid.

In one embodiment, the peptide derivative may be an oligopeptide consisting of 2 to 5, preferably 2 to 4 of sequence units of Xaa-Yaa-Zaa, wherein the N-terminus of the oligopeptide is bound to a fatty acid or an organic acid, and wherein the sequence units forming the oligopeptide may all be the same. In one embodiment, the peptide derivative may be an oligopeptide consisting of 2 to 5, preferably 2 to 4 of sequence units of Xaa-Yaa-Zaa, wherein the N-terminus of the oligopeptide is bound to an acyl group derived from a fatty acid or an organic acid, and wherein the sequence units forming the oligopeptide may all be the same.

In one embodiment, the peptide derivative may be an oligopeptide consisting of 2 to 5, preferably 2 to 4 of sequence units of Xaa-Yaa-Zaa, wherein the N-terminus of the oligopeptide is bound to a fatty acid or an organic acid, and wherein the sequence units forming the oligopeptide may be partially the same. In one embodiment, the peptide derivative may be an oligopeptide consisting of 2 to 5, preferably 2 to 4 of sequence units of Xaa-Yaa-Zaa, wherein the N-terminus of the oligopeptide is bound to an acyl group derived from a fatty acid or an organic acid, and wherein the sequence units forming the oligopeptide may be partially the same.

In one embodiment, the peptide derivative may be an oligopeptide consisting of 2 to 5, preferably 2 to 4 of sequence units of Xaa-Yaa-Zaa, wherein the N-terminus of the oligopeptide is bound to a fatty acid or an organic acid, and wherein the sequence units forming the oligopeptide may not all be the same. In one embodiment, the peptide derivative may be an oligopeptide consisting of 2 to 5, preferably 2 to 4 of sequence units of Xaa-Yaa-Zaa, wherein the N-terminus of the oligopeptide is bound to an acyl group derived from a fatty acid or an organic acid, and wherein the sequence units forming the oligopeptide may not all be the same.

In one embodiment, the peptide derivative may be an amino acid sequence of CWK having a fatty acid or organic acid bound to the N-terminus, CKF having a fatty acid or organic acid bound to the N-terminus, or KCV having a fatty acid or organic acid bound to the N-terminus. In one embodiment, the peptide derivative may be an amino acid sequence of CWK having an acyl group derived from a fatty acid or an organic acid bound to the N-terminus, CKF having an acyl group derived from a fatty acid or an organic acid bound to the N-terminus, or KCV having an acyl group derived from a fatty acid or an organic acid bound to the N-terminus.

In one embodiment, the peptide derivative may be an amino acid sequence of CWK having a palmitic acid bound to the N-terminus, CKF having a palmitic acid bound to the N-terminus, or KCV having a palmitic acid bound to the N-terminus. In one embodiment, the peptide derivative may be palmitoyl CWK, palmitoyl CKF, or palmitoyl KCV. In one embodiment, the peptide derivative may be CWK having a palmitoyl group bound to the N-terminus, CKF having a palmitoyl group bound to the N-terminus, or KCV having a palmitoyl group bound to the N-terminus.

According to one embodiment, by binding the N-terminus of the peptide to a fatty acid or organic acid, the penetration of the peptide into the hair (e.g., capillus, eyebrows, eyelashes) may be enhanced, and the binding affinity of the peptide to the hair (e.g., capillus, eyebrows, eyelashes) may be further enhanced.

In one embodiment, the peptide or peptide derivative according to one aspect of the present disclosure may bind (or adsorb) to at least one selected from the group consisting of the cuticle layer, the cortex, and the CMC layer of the hair (e.g., capillus, eyebrows, eyelashes). In one embodiment, the peptide or peptide derivative according to one aspect of the present disclosure may bind (or adsorb) to a structural protein found in damaged hair (e.g., capillus, eyebrows, eyelashes).

In one embodiment, the peptide or peptide derivative according to one aspect of the present disclosure may increase the tensile strength of the hair (e.g., capillus, eyebrows, eyelashes).

In one embodiment, the peptide or peptide derivative according to one aspect of the present disclosure may increase the denaturation enthalpy of the hair (e.g., capillus, eyebrows, eyelashes). A higher denaturation enthalpy value of the hair means higher strength of the hair.

In one embodiment, the peptide or peptide derivative according to one aspect of the present disclosure may bind to (or adsorb) the cuticle layer, cortex, and/or CMC layer of hair (e.g., capillus, eyebrows, eyelashes) to increase the smoothness and elasticity of the surface.

In one embodiment, the peptide or peptide derivative according to one aspect of the present disclosure may repair the damage to the CMC structure in damaged hair (e.g., capillus, eyebrows, eyelashes), and ultimately improve the strength, smoothness, and elasticity of damaged hair (e.g., capillus, eyebrows, eyelashes).

Composition for Hair Protection, Damaged Hair Repair, or Hair Strengthening

One aspect of the present disclosure provides a composition for hair protection, damaged hair repair, or hair strengthening, comprising the peptides described above, peptide derivatives described above, or a mixture of amino acids.

In one embodiment, the composition for hair protection, damaged hair repair, or hair strengthening according to one aspect of the present disclosure may bind (or adsorb) to at least one selected from the group consisting of the cuticle layer, the cortex, and the CMC layer of the hair. In one embodiment, the composition for hair protection, damaged hair repair, or hair strengthening according to one aspect of the present disclosure may bind (or adsorb) to a structural protein found in damaged hair.

In one embodiment, the composition for hair protection, damaged hair repair, or hair strengthening according to one aspect of the present disclosure may increase the tensile strength of hair.

In one embodiment, the composition for hair protection, damaged hair repair, or hair strengthening according to one aspect of the present disclosure may increase the denaturation enthalpy of hair.

In one embodiment, the composition for hair protection, damaged hair repair, or hair strengthening according to one aspect of the present disclosure may bind (or adsorb) to the cuticle layer, cortex, and/or CMC layer of hair to increase the smoothness and elasticity of the surface.

In one embodiment, the composition for hair protection, damaged hair repair, or hair strengthening according to one aspect of the present disclosure may repair the damage to the CMC structure in damaged hair, and ultimately improve the strength, smoothness, and elasticity of the damaged hair.

In one embodiment, the composition for hair protection, damaged hair repair, or hair strengthening according to one aspect of the present disclosure may be a composition for capillus protection, damaged capillus repair, or capillus strengthening.

In one embodiment, the composition for hair protection, damaged hair repair, or hair strengthening according to one aspect of the present disclosure may a composition for eyebrow protection, damaged eyebrow repair, or eyebrow strengthening.

In one embodiment, the composition for hair protection, damaged hair repair, or hair strengthening according to one aspect of the present disclosure may a composition for eyelash protection, damaged eyelash repair, or eyelash strengthening composition.

1) Composition for Hair Protection, Damaged Hair Repair, or Hair Strengthening—1

One aspect of the present disclosure provides a composition for hair protection, damaged hair repair, or hair strengthening, comprising the above-described peptide or peptide derivative.

The peptide and peptide derivative are the same as described above, so a detailed description thereof is omitted.

In one embodiment, the peptide or peptide derivative may be included in an amount of 0.0001 wt % to 100 wt % or less based on the total weight of the composition, but is not limited thereto. For example, the peptide or peptide derivative may be included in an amount of 0.0001 wt % or more, 0.001 wt % or more, 0.005 wt % or more, 0.01 wt % or more, 0.05 wt % or more, 0.1 wt % or more, 0.5 wt % or more, 1 wt % or more, 5 wt % or more, 10 wt % or more, 15 wt % or more, 20 wt % or more, 25 wt % or more, 30 wt % or more, 35 wt % or more, 40 wt % or more, 45 wt % or more, 50 wt % or more, 55 wt % or more, 60 wt % or more, 65 wt % or more, 70 wt % or more, 75 wt % or more, 80 wt % or more, 85 wt % or more, 90 wt % or more, 95 wt % or more, 99 wt % or more, 100 wt % or more, 0.0001 wt % or less, 0.001 wt % or less, 0.005 wt % or less, 0.01 wt % or less, 0.05 wt % or less, 0.1 wt % or less, 0.5 wt % or less, 1 wt % or less, 5 wt % or less, 10 wt % or less, 15 wt % or less, 20 wt % or less, 25 wt % or less, 30 wt % or less, 35 wt % or less, 40 wt % or less, 45 wt % or less, 50 wt % or less, 55 wt % or less, 60 wt % or less, 65 wt % or less, 70 wt % or less, 75 wt % or less, 80 wt % or less, 85 wt % or less, 90 wt % or less, 95 wt % or less, 99 wt % or less, 100 wt % or less, or a combination thereof (e.g., 0.005 to 0.05 wt %, 0.05 to 0.5 wt %) based on the total weight of the composition, but is not limited thereto.

In one preferred embodiment the peptide or peptide derivate may be included in an amount—based on the total weight of the composition—of 50 wt % or more, 60 wt % or more, 70 wt % or more, 80 wt % or more, 90 wt % or more, 95 wt % or more, 99 wt % or more or 100 wt %, wherein the peptide or oligopeptide or peptide derivate thereof consists of 2 to 5, preferably 2 to 4 of the sequence units of Xaa-Yaa-Zaa, wherein preferably two of Xaa, Yaa and Zaa may be C and K, respectively, wherein, when Xaa and Yaa are C and K, respectively, Zaa is not L, more preferably, wherein two of Xaa, Yaa and Zaa may be C and K, respectively, the remaining one may be selected from the group consisting of W, V, and F, more preferably wherein the peptide is a tripeptide consisting of one sequence unit, wherein the peptide is CKF, CWK, or KCV.

In a preferred embodiment, the peptide which is present in the above-mentioned amounts is the oligopeptide CKFCKF (SEQ ID NO. 1), CKFCKFCKF (SEQ ID NO. 2), CKFCKFCKFCKF (SEQ ID NO: 3), CWKCWK (SEQ ID NO: 4), CWKCWKCWK (SEQ ID NO: 5), CWKCWKCWKCWK (SEQ ID NO: 6), KCVKCV (SEQ ID NO. 7), KCVKCVKCV (SEQ ID NO: 8), KCVKCVKCVKCV (SEQ ID NO: 9), CWKCWKKCLKCLKCV (SEQ ID NO: 18), CKWCWKKCLKCVKCL (SEQ ID NO: 19), CKWKCFCKFCWKKCV (SEQ ID NO: 20), KCFKCFCK-WCKFKCV (SEQ ID NO: 21), or CKFCKWKCFKCVKCF (SEQ ID NO: 22).

Preferably, the peptide derivative having a fatty acid bound to the N-terminus of the above-described peptides, is a peptide derivative having at the N-terminus of the above-described peptide a fatty acid of a C8 to C30 fatty acid, a C9 to C29 fatty acid, a C9 to C28 fatty acid, a C9 to C27 fatty acid, a C9 to C26 fatty acid, a C9 to C25 fatty acid, a C9 to C24 fatty acid, a C10 to C24 fatty acid, a C9 to C23 fatty acid, a C10 to C22 fatty acid, a C11 to C21 fatty acid, a C12 to C20 fatty acid, a C13 to C19 fatty acid, a C14 to C18 fatty acid, or a C15 to C17 fatty acid, wherein more preferably the fatty acid is a C15 to C20 fatty acid, more preferably a C15 to C17 fatty acid, most preferably palmitic acid and/or palmitoleic acid.

Preferably, the peptide derivative having a fatty acid bound to the N-terminus disclosed above, is a peptide derivative having at the N-terminus of the above-described peptide an acyl group derived from a C8 to C30 fatty acid, a C9 to C29 fatty acid, a C9 to C28 fatty acid, a C9 to C27 fatty acid, a C9 to C26 fatty acid, a C9 to C25 fatty acid, a C9 to C24 fatty acid, a C10 to C24 fatty acid, a C9 to C23 fatty acid, a C10 to C22 fatty acid, a C11 to C21 fatty acid, a C12 to C20 fatty acid, a C13 to C19 fatty acid, a C14 to C18 fatty acid, a C15 to C20 fatty acid, or a C15 to C17 fatty acid, wherein more preferably a peptide derivative having an acyl group derived from a C15 to C20 fatty acid, wherein more preferably a peptide derivative having an acyl group derived from a C15 to C17 fatty acid, wherein most preferably a peptide derivative having an acyl group derived from palmitic acid and/or palmitoleic acid.

In one embodiment, the peptide or peptide derivative may be administered to the hair of the subject in an amount of, but not limited to, 0.1 to 100 mg per 1 g of hair. For example, the peptide or peptide derivative may be administered to the hair of the subject in an amount of 0.1 mg or more, 1 mg or more, 2 mg or more, 3 mg or more, 4 mg or more, 5 mg or more, 6 mg or more, 7 mg or more, 8 mg or more, 9 mg or more, 10 mg or more, 11 mg or less, 12 mg or less, 13 mg or less, 14 mg or less, 15 mg or less, 16 mg or less, 17 mg or less, 18 mg or less, 19 mg or less, 20 mg or less, 30 mg or less, 40 mg or less, 50 mg or less, 60 mg or less, 70 mg or less, 80 mg or less, 90 mg or less, 100 mg or less, or a combination thereof (e.g., 1 to 20 mg, 9 to 11 mg) per 1 gram of hair, but is not limited thereto.

In one preferred embodiment the peptide or peptide derivative may be administered to the hair of the subject in an amount of 5 to 20 mg, or 9 to 15 mg.

In one embodiment, the peptide or peptide derivative may be administered once or multiple times to the subject, but is not limited thereto.

In one embodiment, the peptide or peptide derivative may be administered in combination with any other ingredient that may exhibit a hair protection effect, a damaged hair repair effect, or a hair strengthening effect, but is not limited thereto.

In one embodiment, the composition for hair protection, damaged hair repair, or hair strengthening may be a cosmetic composition, a food composition, an oral composition, a non-therapeutic composition, a non-therapeutic oral composition, a pharmaceutical composition, or a composition for external use. For example, the composition may be a cosmetic composition. For example, the composition for external use may be a composition for external use in a skin or a composition for external use in a hair.

In one embodiment, the composition for hair protection, damaged hair repair, or hair strengthening may be formulated with at least one selected from the group consisting of hair shampoo, hair rinse, hair conditioner, hair cream, hair oil, hair lotion, scalp pack, hair tonic, hair mist, hair treatment, ampoule, hair serum, hair mousse, hair wax, hair essence, hair spray, eyebrow serum, eyebrow essence, eyelash serum, and eyelash essence, but is not limited thereto.

In one embodiment, the composition for hair protection, damaged hair repair, or hair strengthening may be a wash-off type (a formulation that is washed off, such as shampoo) or a leave-on type (a formulation that is not washed off, such as hair serum), but is not limited thereto.

The composition for hair protection, damaged hair repair, or hair strengthening according to one aspect of the present disclosure may further comprise ingredients that may be included in cosmetics.

The composition for hair protection, damaged hair repair, or hair strengthening according to one aspect of the present disclosure may further comprise additives such as preservatives, thickeners, viscosity modifiers, stabilizers, pearlizing agents, metal ion sequestrants, cationic surfactants, pH adjusters, fragrances and dyes, which can be readily purchased and used commercially.

In one embodiment, the hair may comprise capillus, eyebrows and/or eyelashes, but is not limited thereto.

2) Composition for Hair Protection, Damaged Hair Repair, or Hair Strengthening—2

In addition, one aspect of the present disclosure provides a composition for hair protection, damaged hair repair, or hair strengthening, comprising at least three amino acids selected from the group consisting of C, K, W, V. L (Leu, leucine) and F.

The use of the composition (cosmetic, food, pharmaceutical or external preparation composition), the formulation, and the additives that may be added to the composition are the same as those described above in '1) Composition for hair protection, damaged hair repair, or hair strengthening—1', and thus a detailed description is omitted.

A composition comprising at least three amino acids according to one aspect of the present disclosure can exhibit a hair protection effect, a damaged hair repair effect, or a hair strengthening effect without a peptide synthesis process. Therefore, it is economically advantageous to use a composition comprising at least three amino acids according to one aspect of the present disclosure for hair protection, damaged hair repair, or hair strengthening.

In one embodiment, the at least three amino acids may be included in an amount of 0.0001 wt % to 100 wt % or less based on the total weight of the composition, but is not limited thereto. For example, the at least three amino acids may be included in an amount of 0.0001 wt % or more, 0.001 wt % or more, 0.005 wt % or more, 0.01 wt % or more, 0.05 wt % or more, 0.1 wt % or more, 0.5 wt % or more, 1 wt % or more, 5 wt % or more, 10 wt % or more, 15 wt % or more, 20 wt % or more, 25 wt % or more, 30 wt % or more, 35 wt % or more, 40 wt % or more, 45 wt % or more, 50 wt % or more, 55 wt % or more, 60 wt % or more, 65 wt % or more, 70 wt % or more, 75 wt % or more, 80 wt % or more, 85 wt % or more, 90 wt % or more, 95 wt % or more, 99 wt % or more, 100 wt % or more, 0.0001 wt % or less, 0.001 wt % or less, 0.005 wt % or less, 0.01 wt % or less, 0.05 wt % or less, 0.1 wt % or less, 0.5 wt % or less, 1 wt % or less, 5 wt % or less, 10 wt % or less, 15 wt % or less, 20 wt % or less, 25 wt % or less, 30 wt % or less, 35 wt % or less, 40 wt % or less, 45 wt % or less, 50 wt % or less, 55 wt % or less, 60 wt % or less, 65 wt % or less, 70 wt % or less, 75 wt % or less, 80 wt % or less, 85 wt % or less, 90 wt % or less, 95 wt % or less, 99 wt % or less, 100 wt % or less, or a combination thereof (e.g., 0.005 to 0.05 wt %, 0.05 to 0.5 wt %) based on the total weight of the composition, but is not limited thereto.

In one preferred embodiment the at least three amino acids may be included in an amount of 0.005 to 0.5 wt %, or 0.05 to 0.5 wt %.

In one embodiment, the composition may comprise C; K; and one of W, V. L or F.

In one embodiment, the composition may consist of C; K; and one of W, V, L or F. In one embodiment, the composition comprises C, K and W.

A composition comprising at least three amino acids selected from the group consisting of C, K, W, V, L and F described above can effectively increase the strength of hair compared to a composition comprising other three or more amino acids.

In one embodiment, the composition may comprise i) C; ii) K; and iii) one of W, V, L or F; in a molar mass ratio of 1:0.1 to 5:0.1 to 5, but is not limited thereto. For example, the composition may comprise i) C; ii) K; and iii) one of W, V, L or F; in a molar mass ratio of 1:0.1 to 5:0.1 to 5, 1:0.1 to 4:0.1 to 4, 1:0.1 to 3:0.1 to 3, 1:0.1 to 2:0.1 to 2, 1:0.5 to 2:0.5 to 2, 1:0.5 to 1.5:0.5 to 2, 1:0.6 to 1.5:0.6 to 2, 1:0.7 to 1.4:0.7 to 1.9, 1:0.8 to 1.3:0.8 to 1.8, 1:0.9 to 1.3:0.9 to 1.7, 1:1 to 1.3:1 to 1.7, 1:1.2 to 1.3:1.6 to 1.7, or 1:1:1, but is not limited thereto.

In one embodiment, the hair may comprise capillus, eyebrows and/or eyelashes, but is not limited thereto.

Method for Hair Protection, Damaged Hair Repair, or Hair Strengthening

One aspect of the present disclosure provides a method for hair protection, damaged hair repair, or hair strengthening, comprising administering a mixture of the aforementioned peptides, peptide derivatives, or amino acids.

In one embodiment, the method for hair protection, damaged hair repair, or hair strengthening according to one aspect of the present disclosure may increase the tensile strength of hair.

In one embodiment, the method for hair protection, damaged hair repair, or hair strengthening is a method for increasing tensile strength of hair.

In one embodiment, the method for hair protection, damaged hair repair, or hair strengthening according to one aspect of the present disclosure may increase the denaturation enthalpy of hair.

In one embodiment, the method for hair protection, damaged hair repair, or hair strengthening according to one aspect of the present disclosure may repair the damage to the CMC structure in damaged hair, and ultimately improve the strength, smoothness, and elasticity of damaged hair.

In one embodiment, the method for hair protection, damaged hair repair, or hair strengthening according to one aspect of the present disclosure may be a method for capillus protection, damaged capillus repair, or capillus strengthening.

In one embodiment, the method for hair protection, damaged hair repair, or hair strengthening according to one aspect of the present disclosure may be a method for eyebrow protection, damaged eyebrow repair, or eyebrow strengthening.

In one embodiment, the method for hair protection, damaged hair repair, or hair strengthening according to one aspect of the present disclosure may be a method for eyelash protection, damaged eyelash repair, or eyelash strengthening.

1) Method for Hair Protection, Damaged Hair Repair, or Hair Strengthening—1

One aspect of the present disclosure provides a method for hair protection, damaged hair repair, or hair strengthening, comprising administering an effective amount of the aforementioned peptide or peptide derivative to a subject in need of hair protection, damaged hair repair, or hair strengthening.

One aspect of the present disclosure provides a method for hair protection, damaged hair repair, or hair strengthening, comprising administering a composition comprising the aforementioned peptide or peptide derivative to a subject in need of hair protection, damaged hair repair, or hair strengthening.

The peptide and peptide derivative are the same as described above, so a detailed description thereof is omitted.

In one embodiment, the subject may be an animal, including a mammal (e.g., a human), but is not limited thereto.

In one embodiment, the subject may be a subject with damaged hair or a subject without damaged hair. In one embodiment, the subject may be a subject whose CMC structure of the hair is damaged due to hair damage.

In the present disclosure, the administration may include an oral administration, transdermal administration, subcutaneous administration, intravenous administration, intraperitoneal administration, intramuscular administration, or topical application, but is not limited thereto, preferably a topical application by applying an effective amount of the aforementioned peptide or peptide derivative to the hair.

In one embodiment, the daily administered amount of the active ingredient may be, but is not limited to, 0.0001 to 10000 mg/kg. In one embodiment, the active ingredient may be administered once a day or in several divided doses. However, it should be understood that the administered amount of the active ingredient should be determined in light of various related factors such as the route of administration, the age, sex, and weight of the subject, and therefore, the administration amount does not limit the scope of the present invention in any way.

In one embodiment, the peptide or peptide derivative may be administered to the hair of the subject in an amount of, but not limited to, 0.1 to 100 mg per 1 g of hair. For example, the peptide or peptide derivative may be administered to the hair of the subject in an amount of 0.1 mg or more, 1 mg or more, 2 mg or more, 3 mg or more, 4 mg or more, 5 mg or more, 6 mg or more, 7 mg or more, 8 mg or more, 9 mg or more, 10 mg or more, 11 mg or less, 12 mg or less, 13 mg or less, 14 mg or less, 15 mg or less, 16 mg or less, 17 mg or less, 18 mg or less, 19 mg or less, 20 mg or less, 30 mg or less, 40 mg or less, 50 mg or less, 60 mg or less, 70 mg or less, 80 mg or less, 90 mg or less, 100 mg or less, or a combination thereof (e.g., 1 to 20 mg, 9 to 11 mg) per 1 gram of hair, but is not limited thereto.

In one preferred embodiment the peptide or peptide derivative may be administered to the hair of subject in an amount of 5 mg to 50 mg, 10 mg to 40 mg or 15 mg to 30 mg.

In one embodiment, the peptide or peptide derivative may be administered to the subject once a day or in several divided doses.

In one embodiment, the peptide or peptide derivative may be administered in combination with any other ingredient that may exhibit a hair protection effect, a damaged hair repair effect, or a hair strengthening effect, but is not limited thereto.

In one embodiment, the hair may comprise capillus, eyebrows and/or eyelashes, but is not limited thereto.

2) Method for Hair Protection, Damaged Hair Repair, or Hair Strengthening—2

In addition, one aspect of the present disclosure provides a method for hair protection, damaged hair repair, or hair strengthening, comprising administering an effective amount of a combination of at least three amino acids selected from the group consisting of C, K, W, V, L (Leu, leucine) and F as an active ingredient to a subject in need of hair protection, damaged hair repair, or hair strengthening.

The subject, administration, administration amount, etc. are the same as those described above in '1) Method for hair protection, damaged hair repair, or hair strengthening—1', and thus a detailed description is omitted.

In one embodiment, administering a combination of at least three amino acids as an active ingredient to a subject may be administering a combination of C; K; and one of W, V, L or F; as an active ingredient to the subject. In one embodiment, administering a combination of at least three amino acids as an active ingredient to a subject may be administering a combination of C, K and W as an active ingredient to a subject.

In one embodiment, administering a combination of at least three amino acids as an active ingredient to a subject may be administering a composition comprising at least three amino acids selected from the group consisting of C, K, W, V, L and F as an active ingredient to a subject. The administering a combination of at least three amino acids as an active ingredient to a subject may be administering a composition comprising comprise C; K; and one of W, V. L or F as an active ingredient to a subject. In one embodiment, administering a combination of at least three amino acids as an active ingredient to a subject may be administering a composition comprising comprise C; K; and F as an active ingredient to a subject.

In one embodiment, i) C: ii) K; and iii) one of W, V, L or F: may be administered to the subject in a molar mass ratio of 1:0.1 to 5:0.1 to 5, but is not limited thereto. For example, i) C; ii) K; and iii) one of W, V, L or F; may be administered to the subject in a molar mass ratio of 1:0.1 to 5:0.1 to 5, 1:0.1 to 4:0.1 to 4, 1:0.1 to 3:0.1 to 3, 1:0.1 to 2:0.1 to 2, 1:0.5 to 2:0.5 to 2, 1:0.5 to 1.5:0.5 to 2, 1:0.6 to 1.5:0.6 to 2, 1:0.7 to 1.4:0.7 to 1.9, 1:0.8 to 1.3:0.8 to 1.8, 1:0.9 to 1.3:0.9 to 1.7, 1:1 to 1.3:1 to 1.7, 1:1.2 to 1.3:1.6 to 1.7, or 1:1:1, but is not limited thereto.

In one embodiment, the combination of at least three amino acids selected from the group consisting of C, K, W, V, L and F may be administered to the subject once or multiple times, but is not limited thereto.

In one embodiment, the combination of at least three amino acids selected from the group consisting of C, K, W, V. L and F may be administered in combination with any other ingredient that may exhibit a hair protection effect, a damaged hair repair effect, or a hair strengthening effect, but is not limited thereto.

In one embodiment, the hair may comprise capillus, eyebrows and/or eyelashes, but is not limited thereto.

Use of a Composition Comprising a Peptide, a Peptide Derivative or an Amino Acid One aspect of the present disclosure provides uses of a composition comprising the aforementioned peptide, peptide derivative or amino acid mixture.

1) Use of a Peptide or Peptide Derivative—1

One aspect of the present disclosure provides a use of the aforementioned peptide for hair protection, damaged hair repair, or hair strengthening.

One aspect of the present disclosure provides a use of the aforementioned peptide derivative for hair protection, damaged hair repair, or hair strengthening.

One aspect of the present disclosure provides a use of the aforementioned peptide for manufacturing a composition for hair protection, damaged hair repair, or hair strengthening.

One aspect of the present disclosure provides a use of the aforementioned peptide derivative for manufacturing a composition for hair protection, damaged hair repair, or hair strengthening.

The peptide and peptide derivative are the same as described above, so a detailed description thereof is omitted.

In one embodiment, the use may be a therapeutic or non-therapeutic use.

In one embodiment, the hair may comprise capillus, eyebrows and/or eyelashes, but is not limited thereto.

2) Use of a Composition Comprising Amino Acids—2

One aspect of the present disclosure provides a use of a composition comprising at least three amino acids selected from the group consisting of C, K, W, V, L and F for hair protection, damaged hair repair, or hair strengthening.

One aspect of the present disclosure provides a use of a composition comprising at least three amino acids selected from the group consisting of C, K, W, V. L and F for manufacturing a composition for hair protection, damaged hair repair, or hair strengthening.

The composition comprising at least three amino acids selected from the group consisting of C, K, W, V. L and F is the same as described above, and thus a detailed description thereof is omitted.

In one embodiment, the hair may comprise capillus, eyebrows and/or eyelashes, but is not limited thereto.

Hereinafter, specific examples will be provided and explained in detail to describe the present invention. The following examples are provided only for the purpose of helping to understand the present invention and are not intended to limit the scope and range of the present invention.

Experimental Example 1. Construction of Tripeptide Candidate Sequences and Measurement of Binding Affinity to Hair After constructing multiple tripeptide candidate sequences composed of arbitrary amino acid sequences, the binding affinity of each of the tripeptide candidate sequences to hair was measured using three-dimensional molecular docking simulations. Tripeptide sequences that exhibited excellent binding affinity were selected as sequences expected to show superior hair protection, damaged hair repair, or hair strengthening effects.

Specifically, among 20 essential amino acids, the amino acids suitable for application to hair were divided into three groups. Group 1 (C) includes cysteine (Cys, C), which is effective in disulfide bonding of hair. Group 2 (HPO) includes alanine (Ala, A), leucine (Leu, L), phenylalanine (Phe, F), proline (Pro, P), valine (Val, V), and tryptophan (Trp, W), which have excellent hair penetration characteristics. Group 3 (POS) consists of sequences that help improve the tensile strength of hair and includes cationic amino acids such as arginine (Arg, R), lysine (Lys, K), and histidine (His, H). According to the arrangement method (9 different cases) of amino acids in Table 1, amino acids included in the three groups (Group 1 (C), Group 2 (HPO), and/or Group 3 (POS)) were arranged in the first, second, and third positions, respectively, to construct tripeptide candidate sequences with various sequence combinations. In Table 1, the "number of amino acids" indicates the number of amino acids that can be placed in the first, second, and third positions. As a result, a total of 216 tripeptide candidate sequences were derived with the one-letter code of the amino acids (expressed in alphabet) (see Table 1).

TABLE 1

| Classification | | First Amino Acid ($1^{st}$) | Second Amino Acid ($2^{nd}$) | Third Amino Acid ($3^{rd}$) | Number of Tripeptide Candidate Sequences | | |
|---|---|---|---|---|---|---|---|
| | | | | | Num | Sum | |
| Case #1 | Group Type | Group1(C) | Group2(HPO) | Group2(HPO) | 36 | 108 | 216 |
| | Number of Amino Acid | 1 | 6 | 6 | | | |
| Case #2 | Group Type | Group2(HPO) | Group1(C) | Group2(HPO) | 36 | | |
| | Number of Amino Acid | 6 | 1 | 6 | | | |
| Case #3 | Group Type | Group2(HPO) | Group2(HPO) | Group1(C) | 36 | | |
| | Number of Amino Acid | 6 | 6 | 1 | | | |
| Case #4 | Group Type | Group1(C) | Group2(HPO) | Group3(POS) | 18 | 54 | |
| | Number of Amino Acid | 1 | 6 | 3 | | | |
| Case #5 | Group Type | Group2(HPO) | Group1(C) | Group3(POS) | 18 | | |
| | Number of Amino Acid | 6 | 1 | 3 | | | |
| Case #6 | Group Type | Group2(HPO) | Group3(POS) | Group1(C) | 18 | | |
| | Number of Amino Acid | 6 | 3 | 1 | | | |

TABLE 1-continued

| | | First Amino | Second Amino | Third Amino | Number of Tripeptide Candidate Sequences | |
|---|---|---|---|---|---|---|
| Classification | | Acid (1ˢᵗ) | Acid (2ⁿᵈ) | Acid (3ʳᵈ) | Num | Sum |
| Case #7 | Group Type | Group1(C) | Group3(POS) | Group2(HPO) | 18 | 54 |
| | Number of Amino Acid | 1 | 3 | 6 | | |
| Case #8 | Group Type | Group3(POS) | Group1(C) | Group2(HPO) | 18 | |
| | Number of Amino Acid | 3 | 1 | 6 | | |
| Case #9 | Group Type | Group3(POS) | Group2(HPO) | Group1(C) | 18 | |
| | Number of Amino Acid | 3 | 6 | 1 | | |

After entering the generated one-letter codes sequentially in an Excel file based on rows, three-dimensional peptide molecular files (*.sd or *.sdf) containing atomic coordination information for the generated one-letter codes were batch created using DS software.

To calculate the binding affinity of the generated three-dimensional peptide molecule files, three-dimensional molecule files (*.pdb) of three types of keratin proteins that are targets of binding were obtained from AlphaFold (alphafold.ebi.ac.uk). Specifically, three-dimensional molecule files (*.pdb) of Keratin 85 (Uniprot code: P78386), Keratin 33b (Uniprot code: Q14525), and Keratin associated protein 3-1 (Uniprot code: Q9BYR8) were used.

Using the CDocker module of Discovery Studio (DS) software under the conditions described in FIG. 1, the binding energy between the three-dimensional peptide molecular files and the binding regions of the three types of keratin proteins was calculated. A lower binding energy indicates a stronger binding affinity.

As a result, among the 216 tripeptide candidate sequences, the tripeptides with binding energies of −50 kcal/mol or less for three types of keratin proteins were CKF, CKW, CWK, KCF, KCL, KCV, etc. Meanwhile, the tripeptide with binding energy of 0 kcal/mol or more and the weakest binding affinity was PCP.

Experimental Example 2. Evaluation of the Efficacy of Amino Acid Combinations First, a mixture was prepared by mixing the amino acid components constituting the tripeptides with the highest binding affinity confirmed in Experimental Example 1 above. Specifically, a mixture (Example 1) was prepared by mixing the amino acid components constituting CWK, a tripeptide with the highest binding affinity, in the molar mass ratio shown in Table 2 below (see Table 2). For comparison, a mixture (Comparative Example 1) was prepared by mixing the amino acid components constituting CPP, a tripeptide with the lowest binding affinity, in the molar mass ratio shown in Table 2 below. The numbers in Table 2 represent the molar mass ratios of the amino acids constituting the mixture.

TABLE 2

| | Component | | | |
|---|---|---|---|---|
| Classification | Cysteine (C) | Lysine (K) | Tryptophan (W) | Proline (P) |
| Mixture of Example 1 | 0.26 | 0.31 | 0.43 | |
| Mixture of Comparative Example 1 | 0.34 | | | 0.66 |

(1) Measurement of Tensile Strength

The compositions in Table 2 above were applied to human hair to compare tensile strength.

Specifically, bleached hair tresses (1 g, manufactured by Beaulax) were prepared. The hair tresses were washed using a basic shampoo without conditioning function, rinsed for 1 minute, and dried for 2 minutes. The dried hair tresses (1 g) were immersed in 100 g of a solution in which the test substance (the mixture of Example 1 or the mixture of Comparative Example 1 in Table 2 above) was dissolved at 0.1 wt % (0.1 wt %) is dissolved in purified water (remaining amount) for about 30 minutes. The immersed hair tresses were rinsed in running water for 1 minute and then naturally dried for more than 12 hours. Thirty hair strands were randomly selected from each hair tresses treated with the test substance. Thirty hair strands were randomly selected from the control hair tresses that were not treated with the test substance. The tensile strength of each selected hair was measured using an MTT175 (manufactured by DiaStron) device.

Figure 2:
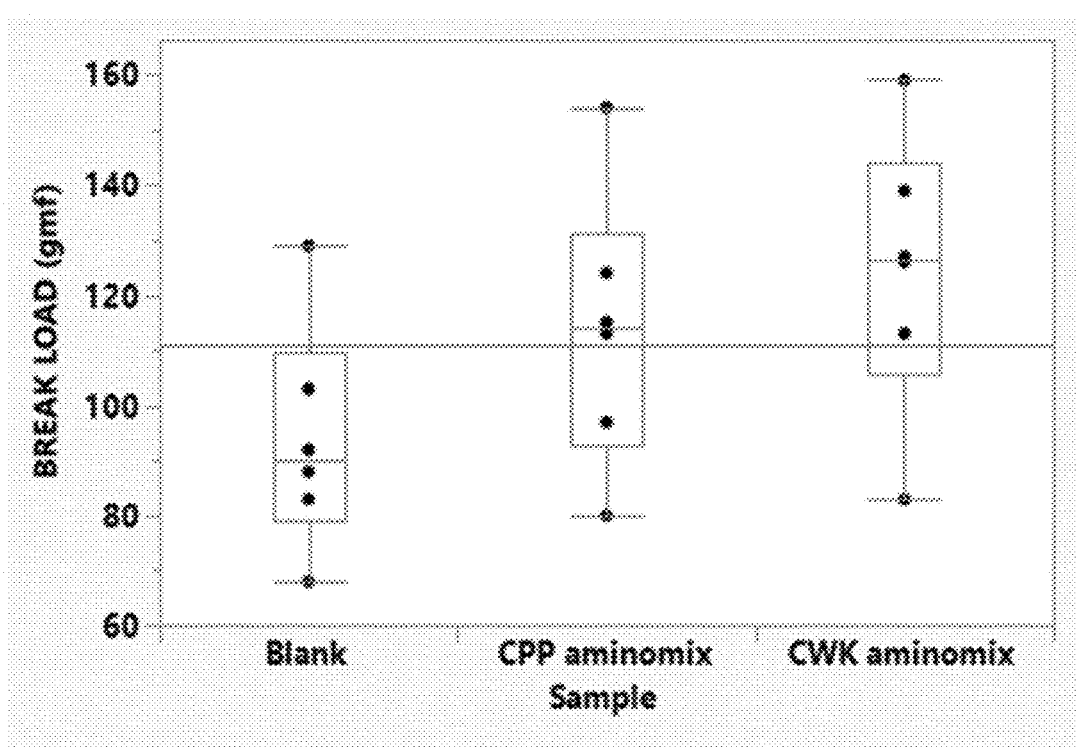
FIG. 2 shows the change in tensile strength of hair by treatment with an amino acid mixture.

As a result, the tensile strength of the hair treated with the mixture of amino acids constituting the tripeptide of CWK significantly increased compared to the bleached hair tresses (see FIG. 2; in FIG. 2, 'Blank' represents the control hair that was not treated with the test substance, 'CWK aminomix' represents the hair treated with the mixture of Example 1, and 'CPP aminomix' represents the hair treated with the mixture of Comparative Example 1). In FIG. 2, the y-axis represents the tensile strength (break load) and the unit is gmf.

(2) Measurement of Denaturation Enthalpy

The denaturation enthalpy of hair structural proteins was compared according to whether or not the test substance was treated using a DSC (Differential Scanning calorimetry)

analyzer. DSC is used as an analysis method to confirm the stability of hair structural proteins. Damage to the hair reduces the stability of hair structural proteins and decreases the enthalpy of denaturation. Specifically, bleached hair tresses (1 g. manufactured by Beaulax) were prepared. The hair tresses were washed using a basic shampoo without a conditioning function, rinsed for 1 minute, and dried for 2 minutes. The dried hair tresses (1 g) were immersed in 100 g of a solution in which the test substance (mixture of Example 1 in Table 2 above) was dissolved at 0.01 wt % (at this time, the solution is a solution in which the mixture of Example 1 (0.01 wt %) is dissolved in purified water (residue) and ethanol (80 wt %)) for 30 minutes. The immersed hair tresses were rinsed in running water for 1 minute and then naturally dried for more than 12 hours. Each treated hair tress was cut into 1 mm lengths, placed in an aluminum high-pressure capsule with 3-5 mg of the cut hair tress and 6-15 mg of distilled water, and combined. After leaving it for more than 12 hours, phase equilibrium was achieved in the high-pressure capsule, and samples (DSC samples) for DSC measurement were prepared. The denaturation enthalpies of the prepared DSC samples were measured using a DSC (Discovery DSC 250, TA Instruments) device (50-190 degrees, 10 degrees/min).

As a result, hair treated with the mixture of amino acids constituting the tripeptide of the CWK sequence significantly increased the denaturation enthalpy of the hair structural protein compared to the control hair (see FIG. 3; in FIG. 3, 'bleach' indicates the control hair that was not treated with the test substance, and 'aminomix' indicates the hair treated with the mixture of Example 1 in Table 2).

Experimental Example 3. Evaluation of Tripeptide
Efficacy—1

Among the tripeptides derived from Experimental Example 1, the peptides with the sequences CKF, CWK, KCL, KCV, and PCP were synthesized in three steps as follows. First, the reaction resin was prepared (2-Cl-(Trt)-Cl resin; CAS No: 27144-18-9) (Step 1). Then, using a peptide synthesizer, a total of three amino acids were coupled by adding single amino acids in the form of Fmoc (fluorenylmethoxycarbonyl protecting group)-amino acid-OH (Step 2). A cleavage solution was added to the coupled substances to precipitate and recover the peptides (Step 3).
(1) Measurement of Tensile Strength
The tensile strength was compared by applying the test substance (the above 5 types of tripeptides) to the hair using the same method as in 'Experimental Example 2. (1) Measurement of tensile strength'.

Specifically, bleached hair tresses (1 g, manufactured by Beaulax) were prepared. The hair tresses were washed using a basic shampoo without conditioning function, rinsed for 1 minute, and dried for 2 minutes. The dried hair tresses (1 g) were immersed in 100 g of a solution in which the test substance (synthesized tripeptide) was dissolved at 0.01 wt % (wherein the solution is a solution in which the test substance (0.01 wt %) is dissolved in purified water (residue) and ethanol (80 wt %)) for about 30 minutes. The immersed hair tresses were rinsed in running water for 1 minute and then naturally dried for more than 12 hours. Thirty hair strands were randomly selected from each hair tresses treated with the test substance. Thirty hair strands were randomly selected from the control hair tresses that were not treated with the test substance. The tensile strength of each selected hair was measured using an MTT175 (manufactured by DiaStron) device.

As a result, the tensile strength of the hair treated with CKF, CWK, KCL, and KCV significantly increased compared to the control bleached hair tresses. On the other hand, the degree of increase in the tensile strength of the hair treated with PCP was not significant (see FIG. 4; in FIG. 4, 'CKF' represents hair treated with CKF tripeptide, 'CTL-BLEACH' represents control hair that was not treated with the test substance, 'CWK' represents hair treated with CWK tripeptide, 'KCL' represents hair treated with KCL tripeptide, 'KCV' represents hair treated with KCV tripeptide, and 'PCP' represents hair treated with PCP tripeptide).
(2) Measurement of Denaturation Enthalpy
The denaturation enthalpy was measured by the same method as in 'Experimental Example 2. (2) Measurement of denaturation enthalpy', but the denaturation enthalpy was compared by applying applied CWK tripeptide as a test substance to hair. As a result, hair treated with CWK tripeptide significantly increased the denaturation enthalpy of hair structural proteins compared to the control group hair (see FIG. 3; in FIG. 3, 'bleach' represents control hair that was not treated with the test substance, and 'CWK' represents hair treated with CWK tripeptide).

Experimental Example 4. Evaluation of the Efficacy
of Tripeptides with Fatty Acids Bound to the
N-Terminus (1) Measurement of Binding Affinity with Keratin Proteins
A molecular file was created by adding palmitic acid to the sequences of the four tripeptides (CKF, CWK, KCL, and KCV) whose effects were confirmed through 'Experimental Example 3', and molecular docking simulation was performed under the same conditions as Experimental Example 1 above to measure the binding energy of the tripeptides with added palmitic acid to the three types of keratin protein.
As a result, the binding energy of the tripeptides with added palmitic acid to the three types of keratin protein was lower than that of the tripeptides without added palmitic acid. Through this, it was confirmed that the tripeptides with added palmitic acid had a higher binding affinity to hair.
(2) Measurement of Tensile Strength
The tensile strength was measured after palmitic acid was covalently bound to three tripeptides (CKF, CWK, and KCV) among the tripeptides whose effect was confirmed through 'Experimental Example 4 (1) Measurement of binding affinity with keratin proteins'.
Specifically, the tripeptide was synthesized using the same method as the peptide synthesis method of 'Experimental Example 3' above, but palmitic acid was added to the N-terminus of the peptide (reagents: HBTU (Hexafluorophosphate Benzotriazole), NMM (N-Methylmorpholine), DMF (Dimethylformamide), 1 hour at room temperature, concentration 0.3 M), and a tripeptide with palmitic acid covalently bonded to the N-terminus (i.e., palmitoyl tripeptide) was synthesized. After that, the test substance (tripeptide with palmitic acid covalently bonded to the N-terminus) was applied to the hair and the tensile strength was compared using the same method as in 'Experimental Example 3. (1) Measurement of tensile strength'.
As a result, the tensile strength of hair treated with a tripeptide having palmitic acid covalently bonded to the N-terminus was significantly increased compared to the control group, bleached hair tresses (see FIG. 5, in FIG. 5, 'aminomix' represents hair treated with the mixture of Example 1 in Table 2, 'Con' represents control hair not treated with the test substance, 'CWK' represents hair treated with CWK tripeptide, 'pal-CKF' represents hair treated with CKF (palmitoyl-CKF) having palmitic acid covalently bonded to the N-terminus, 'pal-CWK' represents hair treated with CWK (palmitoyl-CWK) having palmitic acid covalently bonded to the N-terminus, 'pal-KCV' represents hair treated with KCV (palmitoyl-KCV) having palmitic acid covalently bonded to the N-terminus, and 'palmitic acid' represents hair treated with palmitic acid). Additionally, hair treated with a tripeptide having palmitic acid covalently bonded to the N-terminus exhibited higher tensile strength than hair treated with a tripeptide having no palmitic acid covalently bonded to the N-terminus or hair treated with an amino acid mixture.

(3) Measurement of Denaturation Enthalpy

The denaturation enthalpy was measured by the same method as in 'Experimental Example 2. (2) Measurement of denaturation enthalpy', but the denaturation enthalpy was compared by applying a tripeptide with palmitic acid covalently bonded to the N-terminus (i.e. palmitoyl tripeptide) to hair as the test substance.

As a result, hair treated with a tripeptide having palmitic acid covalently bound to the N-terminus significantly increased the denaturation enthalpy of hair structural proteins compared to the control hair (see FIG. 3; in FIG. 3, 'palmitic acid' represents hair treated with palmitic acid, 'pal-CWK' represents hair treated with CWK (palmitoyl-CWK) having palmitic acid covalently bound to the N-terminus, 'pal-KCV' represents hair treated with KCV (palmitoyl-KCV) having palmitic acid covalently bound to the N-terminus, and 'pal-CKF' represents hair treated with CKF (palmitoyl-CKF) having palmitic acid covalently bound to the N-terminus).

(4) Confirmation of Penetration and Binding Effect in Hair Using Confocal Microscopy A green fluorescent substance (FITC; Fluorescein isothiocyanate) was conjugated to palmitoyl-CWK, a tripeptide (i.e., palmitoyl tripeptide) covalently bound to palmitic acid at the N-terminus (fluorescent labeling) and applied to hair. After that, the change in hair structure that affects the increase in hair tensile strength was confirmed by comparing the colored areas using a confocal microscopy.

As a result, as shown in FIG. 6, the hair cuticle, hair cortex, and CMC areas were colored green (indicated in gray in FIG. 6), indicating that palmitoyl tripeptide was strongly bound to the hair cuticle, hair cortex, and CMC (see the left picture of FIG. 6; gray). These results show a similar trend to the results of applying Nile Red, a fat-soluble fluorescent substance, to hair (see the right picture of FIG. 6; gray).

Meanwhile, for comparison of hair penetration routes, the water-soluble fluorescent substance 5-(4-Dimethylamino-benzylidene) rhodanine was applied to the hair, and the colored area (indicated in gray in FIG. 7) was confirmed using a confocal microscope. As a result, as shown in FIG. 7, the water-soluble fluorescent substance barely remained in the cuticle layer on the hair surface and did not fill the lost area of CMC inside the hair (see FIG. 7; gray).

The above experimental results serve as the basis for the fact that palmitoyl tripeptide targets CMC inside the hair through a different penetration route from water-soluble substances, thereby enhancing the structural function of the hair.

Experimental Example 5. Evaluation of the Efficacy of Oligopeptides with Combined Tripeptide Sequences Three-dimensional molecular files (molecular structure files) of i) an oligopeptide repeating one sequence among the tripeptide sequences with the highest binding affinity confirmed in Experimental Example 1 above (12mer; AP 3mer*4 (repeat); for example CWKCWKCWKCWK (SEQ ID NO. 6)) and ii) an oligopeptide randomly combining two or more sequences among the tripeptide sequences with the highest binding affinity confirmed in Experimental Example 1 above (12mer; AP 3mer*4 (random)) were created. And the binding affinity of each peptide molecular file to hair was measured. Using the same method and conditions as Experimental Example 1 above, three-dimensional molecular files of the peptides to be tested were created, and molecular docking simulation was performed using the created molecular files to measure the binding affinity to hair.

For comparison, molecular files of a known third-party peptides or a similar peptide thereof were created, and the binding affinity to hair was confirmed (see FIG. 8). Specifically, (a) amino acids (arginine, cysteine, and glycine) known to constitute the known tetrapeptide-97 (Caregen; INCI Monograph ID: 37801) were randomly combined to generate molecular files of all possible tetrapeptides. Then, the binding affinity to hair was measured using each of the molecular files of all generated tetrapeptides. In addition, (b) amino acids (cysteine, glycine, isoleucine, phenylalanine, serine, threonine, and valine) known to constitute the known oligopeptide sh-Oligopeptide-78 (INCI Monograph ID: 28756) were randomly combined to generate molecular files of all possible oligopeptides (total number of amino acids: 13). In addition, (c) molecular files of eight known oligopeptides (CCQSSCCKPSC (PepA; SEQ ID NO: 10), CVSS-CCKPQCC (PepB; SEQ ID NO: 11), PIYCRRTCYH (PepC; SEQ ID NO: 12), DCKLPCNPCA (PepD; SEQ ID NO. 13), CLPCLPAASC (PepE; SEQ ID NO: 14), CEPAICEPSC (PepF; SEQ ID NO: 15), CQCSCCKPYCS (PepG; SEQ ID NO: 16), GGVCGPSPPCITT (KP; SEQ ID NO: 17)) were generated. Then, the binding affinity of all oligopeptides generated as molecular files in (b) and (c) above to hair was measured.

In FIG. 8, 'CG 4mer' is a peptide showing the highest binding affinity among all tetrapeptides generated as molecular files in (a) above. 'CG 4mer*3' is an oligopeptide (total number of amino acids: 12) with three repeats of the sequence of the peptide showing the highest binding affinity among all tetrapeptides generated as molecular files in (a) above. 'K18 (13mer)' is the peptide showing the highest binding affinity among all oligopeptides generated as molecular files in (b) and (c) above. 'AP 3mer' is the peptide showing the highest binding affinity among the tripeptide candidate sequences of Experimental Example 1 described above. 'AP 3mer-Pal' is the peptide having the highest binding affinity to hair among the molecular files of peptide with palmitic acid added to the N-terminus of the tripeptide candidate sequence of Experimental Example 1 described above. 'AP 3mer*4 (repeat)' is the peptide having the highest binding affinity to hair among the oligopeptides in which any one sequence of the tripeptide candidate sequences of Experimental Example 1 described above is repeated four times. 'AP 3mer*4 (random)' is the oligopeptide showing the highest binding affinity among the oligopeptides in which two or more sequences of the tripeptide candidate sequences of Experimental Example 1 above are randomly combined.

As shown in FIG. 8, the oligopeptides (AP 3mer*4 (repeat), AP 3mer*4 (random) in which the tripeptide sequence of the Example is repeated or combined exhibited a binding affinity of up to 150% compared to the known third-party peptide or similar peptide (see FIG. 8). The y-axis of FIG. 8 represents a negative value. Therefore, it can be seen that the higher the value of the y-axis in FIG. 8, the lower the binding energy and the higher the binding affinity. Through this, it can be seen that the oligopeptide of the Example can bind to hair more effectively than the known third-party peptide and improve the strength of the hair.

Meanwhile, although the tripeptide (AP 3mer) and palmitoyl tripeptide (AP 3mer-Pal) had lower binding affinity to hair compared to oligopeptides (AP 3mer*4 (repeat), AP 3mer*4 (random)) in which the tripeptide sequence was repeated or combined, they exhibited a significant hair strength improvement effect compared to the untreated control group as disclosed in Experimental Examples 1 to 4. At the same time, since tripeptide (AP 3mer) and palmitoyl tripeptide (AP 3mer-Pal) can be easily synthesized due to their short sequence lengths, they have advantages in terms of time and cost.

Experimental Example 6. Evaluation of Tripeptide Efficacy—2

The tripeptide of the KCV sequence was synthesized using the same method as disclosed in Experimental Example 3 above, and its efficacy was evaluated.

(1) Preparation of Hair Simulating Eyebrow

In order to confirm that the test substance exhibits the same effect on eyebrows, an additional experiment was conducted using hair simulating eyebrows. Meanwhile, as described above, the structure and composition of eyebrows are no different from those of hair in other parts of the body (e.g., capillus), and the basic structure/composition of hair follicles in the body are the same, so the effect of the test substance on hair in other parts of the body other than eyebrows will be the same on eyebrows and/or eyelashes.

Specifically, since it is difficult to obtain eyebrows to be used for evaluation directly from a living body, human hair corresponding to the thickness of eyebrows was selected through Fibra.one (manufactured by DiaStron). The length was prepared to a level that can be applied to a machine measuring tensile strength. Heat-treated hair was prepared by applying pressure by hand at 160° C. 20 times with a hair straightener to the prepared human hair tresses. Hair that had not been heat-treated was prepared as a control group (untreated hair in FIGS. 9 and 11). In Experimental Example 6, the untreated hair was not treated with the test substance.

After that, the heat-treated hair tresses were treated with the test substance, KCV (KCV-treated hair in FIGS. 9 and 11). Specifically, the prepared tresses (1 g, manufactured by Beaulax) were washed using a basic cleanser without conditioning function, rinsed for 1 minute, and dried for 2 minutes. The dried tresses (1 g) were immersed in 100 g of a solution in which the test substance was dissolved at 0.01 wt % for about 30 minutes, wherein the solution is a solution in which the test substance (0.01 wt %) is dissolved in purified water (remaining amount). The immersed tresses were rinsed in running water for 1 minute and then naturally dried for more than 12 hours. In order to compare the effects of KCV treatment, hair that was washed and dried under the same conditions as above but was not treated with the test substance (heat-damaged hair in FIGS. 9 and 11) was prepared.

(2) Measurement of Tensile Strength

The tensile strength of KCV-treated hair, heat-damaged hair, and untreated hair was compared using the same method as in 'Experimental Example 2. (1) Measurement of tensile strength'.

Specifically, 30 hair strands were randomly selected from each tress (KCV-treated hair) treated with the test substance. 30 hair strands were randomly selected from the control group (heat-damaged hair and untreated hair, respectively) hair tresses that were not treated with the test substance. The tensile strength of each selected hair was measured using a Fibra.one (manufactured by DiaStron).

As a result, the tensile strength of the KCV-treated hair tresses treated with KCV after heat treatment significantly increased compared to the heat-damaged hair tresses (see FIG. 9, in FIG. 9, 'KCV-treated hair' means hair treated with KCV tripeptide after heat treatment, 'untreated hair' means control hair that was not treated with heat treatment and the test substance, and 'heat-damaged hair' means heat-treated hair). In FIG. 9, the y-axis is the tensile strength (break load) per area, and the unit is $gmf/\mu m^2$.

(3) Elasticity Measurement

The elasticity of KCV-treated hair, heat-damaged hair, and untreated hair was compared. Elasticity was defined as the horizontal resistance of hair, and elasticity was measured through each step of [Method for Measuring Hair Elasticity] below (see FIG. 10).

[Method for Measuring Hair Elasticity]

(i) Place the module (M) on which the eyebrows are mounted on a horizontally movable rail. (ii) Place a total of 10 hair strands (15 mm) vertically on the clip fixed to the module (M). (iii) Move the module (M) toward the fixed micro-manometer (DS2-5N, OPTECH). (iv) Measure the value of the force transmitted by the hair bundle to the tip of the micro-manometer.

As a result, the elasticity of the KCV-treated hair tresses treated with KCV after heat treatment significantly increased compared to the heat-damaged hair tresses (see FIG. 11; in FIG. 11, 'KCV-treated hair' means hair treated with KCV tripeptide after heat treatment, 'untreated hair' means control hair that was not treated with heat treatment and the test substance, and 'heat-damaged hair' means heat-treated hair). In FIG. 11, the y-axis is elasticity and the unit is $10^{-3}$ N.

The present disclosure is further illustrated by the following embodiments, which do not limit the scope of the claims.

Embodiment 1. A peptide comprising one or more amino acid sequence units of Xaa-Yaa-Zaa:

wherein the Xaa, Yaa, and Zaa are each independently selected from the group consisting of C (cysteine), K (lysine), W (tryptophan), V (valine), L (leucine) and F (phenylalanine), and wherein the Xaa, Yaa, and Zaa are all different and wherein, when Xaa and Yaa are C and K, respectively, Zaa is not L.

Embodiment 2. The peptide according to Embodiment 1, wherein two of the Xaa, Yaa, and Zaa are C and K, respectively, and wherein, when Xaa and Yaa are C and K, respectively, Zaa is not L.

Embodiment 3 The peptide according to any one of Embodiments 1 to 2, wherein the peptide is a tripeptide consisting of one sequence unit of Xaa-Yaa-Zaa.

Embodiment 4. The peptide according to any one of Embodiments 1 to 3, wherein the peptide is an oligopeptide consisting of 2 to 4 of the sequence units of Xaa-Yaa-Zaa, and the sequence units forming the oligopeptide are all identical, partially identical, or all different.

Embodiment 5. The peptide according to any one of Embodiments 1 to 4, wherein the peptide is selected from CKF, CWK, KCV, CKFCKF (SEQ ID NO: 1), CKFCKFCKF (SEQ ID NO: 2), CKFCKFCKFCKF (SEQ ID NO: 3), CWKCWK (SEQ ID NO: 4), CWKCWKCWK (SEQ ID NO: 5), CWKCWKCWKCWK (SEQ ID NO: 6), KCVKCV (SEQ ID NO: 7), KCVKCVKCV (SEQ ID NO: 8), KCVKCVKCVKCV (SEQ ID NO: 9), CWKCWKKCLKCLKCV (SEQ ID NO: 18), CKWCWKKCLKCVKCL (SEQ ID NO: 19), CKWKCFCKFCWKKCV (SEQ ID NO: 20), KCFKCFCKWCKFKCV (SEQ ID NO: 21), or CKFCKWKCFKCVKCF (SEQ ID NO: 22).

Embodiment 6. A peptide derivative in which an acyl group derived from a fatty acid or an organic acid is bound to the N-terminus of the peptide of any one of Embodiments 1 to 5.

Embodiment 7. The peptide derivative according to Embodiment 6, wherein the fatty acid is a C10 to C30 fatty acid, preferably a C15 to C20 fatty acid, more preferably a C15 to C17 fatty acid.

Embodiment 8. The peptide derivative according to any one of Embodiments 6 to 7, wherein the fatty acid is at least one selected from the group consisting of palmitic acid, stearic acid, arachidic acid, palmitoleic acid, oleic acid and eicosenoic acid more preferably palmitic acid.

Embodiment 9. The peptide derivative according to any one of Embodiments 6 to 8, wherein the peptide derivative is CKF having a palmitoyl group bound to the N-terminus, CWK having a palmitoyl group bound to the N-terminus, or KCV having a palmitoyl group bound to the N-terminus.

Embodiment 10. A method for hair protection, damaged hair repair, or hair strengthening, comprising administering a composition comprising the peptide of any one of Embodiments 1 to 5.

Embodiment 11. A method for hair protection, damaged hair repair, or hair strengthening, comprising administering a composition comprising the peptide derivative of any one of Embodiments 6 to 9.

Embodiment 12. A method for hair protection, damaged hair repair, or hair strengthening, comprising administering a composition comprising at least three amino acids selected from the group consisting of C, K, W, V, L (leucine), and F.

Embodiment 13. The method for hair protection, damaged hair repair, or hair strengthening according to Embodiment 12, wherein the composition comprises C; K; and one of W, V, L, or F.

Embodiment 14. The method for hair protection, damaged hair repair, or hair strengthening according to Embodiment 12, wherein the composition consists of C; K; and one of W, V, L, or F.

Embodiment 15. The method for hair protection, damaged hair repair, or hair strengthening according to any one of Embodiments 12 to 14, wherein the molar mass ratio of C; K; and one of W, V, L, or F is 1:0.1 to 5:0.1 to 5.

[SEQ ID NO.]
SEQ ID NO: 1 (Peptide sequence of one embodiment):
CKFCKF

SEQ ID NO: 2 (Peptide sequence of one embodiment):
CKFCKFCKF

SEQ ID NO: 3 (Peptide sequence of one embodiment):
CKFCKFCKFCKF

SEQ ID NO: 4 (Peptide sequence of one embodiment):
CWKCWK

SEQ ID NO: 5 (Peptide sequence of one embodiment):
CWKCWKCWK

SEQ ID NO: 6 (Peptide sequence of one embodiment):
CWKCWKCWKCWK

SEQ ID NO: 7 (Peptide sequence of one embodiment):
KCVKCV

SEQ ID NO: 8 (Peptide sequence of one embodiment):
KCVKCVKCV

SEQ ID NO: 9 (Peptide sequence of one embodiment):
KCVKCVKCVKCV

SEQ ID NO: 18 (Peptide sequence of one embodiment):
CWKCWKKCLKCLKCV

SEQ ID NO: 19 (Peptide sequence of one embodiment):
CKWCWKKCLKCVKCL

SEQ ID NO: 20 (Peptide sequence of one embodiment):
CKWKCFCKFCWKKCV

SEQ ID NO: 21 (Peptide sequence of one embodiment):
KCFKCFCKWCKFKCV

SEQ ID NO: 22 (Peptide sequence of one embodiment):
CKFCKWKCFKCVKCF

SEQ ID NO: 10 (PepA peptide sequence):
CCQSSCCKPSC

SEQ ID NO: 11 (PepB peptide sequence):
CVSSCCKPQCC

SEQ ID NO: 12 (PepC peptide sequence):
PIYCRRTCYH

SEQ ID NO: 13 (PepD peptide sequence):
DCKLPCNPCA

SEQ ID NO: 14 (PepE peptide sequence):
CLPCLPAASC

SEQ ID NO: 15 (PepF peptide sequence):
CEPAICEPSC

SEQ ID NO: 16 (PepG peptide sequence):
CQCSCCKPYCS

SEQ ID NO: 17 (KP peptide sequence):
GGVCGPSPPCITT

What is claimed is:

1. A hair cosmetic composition for hair protection, damaged hair repair, or hair strengthening, comprising:
   a peptide or a peptide derivative in an amount effective to protect hair, repair damaged hair, or strengthen hair,
   wherein the peptide is KCV (Lys-Cys-Val), and
   wherein the peptide derivative is KCV having a palmitoyl group bound to the N-terminus (palmitoyl-Lys-Cys-Val),
   wherein the hair is head hair, eyebrows, and/or eyelashes; and wherein the hair cosmetic composition is selected from the group consisting of hair shampoo, hair rinse, hair conditioner, hair cream, hair oil, hair lotion, hair tonic, hair mist, hair treatment, hair serum, hair mousse, hair wax, hair essence, hair spray, eyebrow serum, eyebrow essence, eyelash serum, and eyelash essence.

2. The hair cosmetic composition according to claim 1, wherein the effective amount of the peptide or the peptide derivative is 5 to 20 mg per 1 g of hair.

* * * * *